(12) United States Patent
Singh et al.

(10) Patent No.: US 11,033,333 B2
(45) Date of Patent: Jun. 15, 2021

(54) PLATE SELECTION USER INTERFACE AND DESIGN TOOL WITH DATABASE

(71) Applicant: Stryker European Holdings I, LLC, Kalamazoo, MI (US)

(72) Inventors: Manoj Kumar Singh, Mahwah, NJ (US); Anup Kumar, Gurgaon (IN)

(73) Assignee: Stryker European Holdings I, LLC, Kalamazoo, MI (US)

( * ) Notice: Subject to any disclaimer, the term of this patent is extended or adjusted under 35 U.S.C. 154(b) by 228 days.

(21) Appl. No.: 15/910,120

(22) Filed: Mar. 2, 2018

(65) Prior Publication Data

US 2018/0289423 A1      Oct. 11, 2018

Related U.S. Application Data

(60) Provisional application No. 62/482,422, filed on Apr. 6, 2017.

(51) Int. Cl.
*A61B 34/10*      (2016.01)
*A61B 17/15*      (2006.01)
(Continued)

(52) U.S. Cl.
CPC ............ *A61B 34/10* (2016.02); *A61B 17/151* (2013.01); *A61B 17/152* (2013.01); *A61B 17/80* (2013.01);
(Continued)

(58) Field of Classification Search
CPC . A61B 17/80–17/8095; A61B 17/1775; A61B 34/10–2034/108
See application file for complete search history.

(56) References Cited

U.S. PATENT DOCUMENTS

| 2,825,329 A | 3/1958 | Caesar |
| 3,709,218 A | 1/1973 | Halloran |

(Continued)

FOREIGN PATENT DOCUMENTS

WO      2016112469 A1      7/2016

OTHER PUBLICATIONS

Extended European Search Report and Written Opinion for EP Application No. 18178063.6, dated Apr. 8, 2019.

(Continued)

*Primary Examiner* — Zade Coley
(74) *Attorney, Agent, or Firm* — Lerner, David, Littenberg, Krumholz & Mentlik, LLP

(57) ABSTRACT

Described herein are systems and methods in which a surgeon can use computer-implemented deformity assessment and correction tools to create 3D models of a bone. To ensure adequate healing, a surgeon may choose to use a prefabricated bone plate, a semi-customized bone plate, or a fully-customized bone plate to hold first and second bone portions in a corrected position. To select the appropriate prefabricated bone plate, the surgeon may identify three landmark locations on the first and second bone portions corresponding to desired fixation hole locations on the bone plate. The surgeon can then use a software application to evaluate multiple bone plate designs in a library and compare the average proximity of the landmark locations to fixation hole locations on each of the bone plate designs. Then, the surgeon can determine which bone plate design best fits the patient anatomy based on his comparison.

18 Claims, 32 Drawing Sheets

(51) Int. Cl.
  *A61B 17/80* (2006.01)
  *A61B 17/56* (2006.01)
  *A61B 17/17* (2006.01)

(52) U.S. Cl.
  CPC ...... *A61B 17/8061* (2013.01); *A61B 17/8095* (2013.01); *A61B 17/1775* (2016.11); *A61B 2017/568* (2013.01); *A61B 2034/108* (2016.02)

(56) References Cited

U.S. PATENT DOCUMENTS

| | | | |
|---|---|---|---|
| 3,900,025 | A | 8/1975 | Barnes, Jr. |
| 4,235,428 | A | 11/1980 | Davis |
| 4,719,907 | A | 1/1988 | Bank et al. |
| 4,969,886 | A | 11/1990 | Cziffer et al. |
| 5,139,550 | A | 8/1992 | Nicholls et al. |
| 5,529,075 | A | 6/1996 | Clark |
| 5,916,219 | A | 6/1999 | Matsuno et al. |
| 5,921,986 | A | 7/1999 | Bonutti |
| 6,183,477 | B1 | 2/2001 | Pepper |
| 6,221,073 | B1 | 4/2001 | Weiss et al. |
| 6,287,307 | B1 | 9/2001 | Abboudi |
| 6,932,818 | B2 | 8/2005 | Behrens |
| 7,090,676 | B2 | 8/2006 | Huebner et al. |
| 7,147,640 | B2 | 12/2006 | Huebner et al. |
| 7,153,309 | B2 | 12/2006 | Huebner et al. |
| 7,189,237 | B2 | 3/2007 | Huebner |
| 7,198,628 | B2 | 4/2007 | Ondrla et al. |
| 7,235,079 | B2 | 6/2007 | Jensen et al. |
| 7,326,212 | B2 | 2/2008 | Huebner |
| 7,347,861 | B2 | 3/2008 | Johnstone |
| 7,410,489 | B2 | 8/2008 | Dakin et al. |
| 7,537,596 | B2 | 5/2009 | Jensen |
| 7,537,603 | B2 | 5/2009 | Huebner et al. |
| 7,537,604 | B2 | 5/2009 | Huebner |
| 7,578,825 | B2 | 8/2009 | Huebner |
| 7,621,920 | B2 | 11/2009 | Claypool et al. |
| 7,635,365 | B2 | 12/2009 | Ellis et al. |
| 7,648,508 | B2 * | 1/2010 | Lutz ................ A61B 17/02 606/281 |
| 7,658,741 | B2 | 2/2010 | Claypool et al. |
| 7,704,251 | B2 | 4/2010 | Huebner et al. |
| 7,717,945 | B2 | 5/2010 | Jensen et al. |
| 7,794,467 | B2 | 9/2010 | McGinley et al. |
| 7,837,717 | B2 | 11/2010 | Deffenbaugh et al. |
| 7,857,836 | B2 | 12/2010 | Huebner et al. |
| 7,914,532 | B2 | 3/2011 | Shaver et al. |
| 7,927,332 | B2 | 4/2011 | Huebner et al. |
| 7,955,388 | B2 | 6/2011 | Jensen et al. |
| 8,043,297 | B2 | 10/2011 | Grady, Jr. et al. |
| 8,187,308 | B2 | 5/2012 | Mullaney et al. |
| 8,231,627 | B2 | 7/2012 | Huebner et al. |
| 8,231,662 | B2 | 7/2012 | Huebner |
| 8,262,706 | B2 | 9/2012 | Olms et al. |
| 8,313,492 | B2 | 11/2012 | Wong et al. |
| 8,328,809 | B2 | 12/2012 | Wenk et al. |
| 8,372,078 | B2 | 2/2013 | Collazo |
| 8,398,678 | B2 | 3/2013 | Baker et al. |
| 8,398,717 | B2 | 3/2013 | Kleinman |
| 8,403,966 | B2 | 3/2013 | Ralph et al. |
| 8,425,574 | B2 | 4/2013 | Huebner et al. |
| 8,425,575 | B2 | 4/2013 | Huebner et al. |
| 8,475,504 | B2 | 7/2013 | Gillard et al. |
| 8,500,745 | B2 | 8/2013 | Kuenzi et al. |
| 8,506,597 | B2 | 8/2013 | Kaiser et al. |
| 8,523,919 | B2 | 9/2013 | Huebner et al. |
| 8,579,900 | B2 | 11/2013 | Hsu |
| 8,585,744 | B2 | 11/2013 | Duggal et al. |
| 8,628,531 | B2 | 1/2014 | Ritchey et al. |
| 8,652,142 | B2 * | 2/2014 | Geissler ............. A61B 17/15 606/87 |
| 8,685,030 | B2 | 4/2014 | Gotte et al. |
| 8,764,763 | B2 | 7/2014 | Wong et al. |
| 8,821,580 | B2 | 9/2014 | DaSilva |
| 8,886,496 | B2 | 11/2014 | Graumann |
| 9,060,790 | B2 | 6/2015 | Wayne et al. |
| 9,186,163 | B2 | 11/2015 | Cleveland et al. |
| 9,241,744 | B2 | 1/2016 | Blake et al. |
| 9,308,033 | B2 | 4/2016 | Huebner et al. |
| 9,320,553 | B2 | 4/2016 | Katrana et al. |
| 9,339,279 | B2 | 5/2016 | Dubois et al. |
| 9,370,386 | B2 | 6/2016 | Galm et al. |
| 9,402,636 | B2 | 8/2016 | Collazo |
| 9,414,871 | B2 | 8/2016 | Huebner et al. |
| 9,414,873 | B2 | 8/2016 | Graham et al. |
| 9,474,539 | B2 | 10/2016 | Catanzarite et al. |
| 2003/0135212 | A1 | 7/2003 | Chow |
| 2004/0116930 | A1 * | 6/2004 | O'Driscoll ......... A61B 17/8061 606/281 |
| 2005/0216010 | A1 | 9/2005 | Michelson |
| 2005/0234472 | A1 | 10/2005 | Huebner |
| 2005/0273112 | A1 * | 12/2005 | McNamara ............ A61B 17/15 606/87 |
| 2006/0015102 | A1 | 1/2006 | Toullec et al. |
| 2006/0195198 | A1 | 8/2006 | James |
| 2006/0241592 | A1 | 10/2006 | Myerson et al. |
| 2006/0285931 | A1 | 12/2006 | Dean |
| 2007/0225715 | A1 | 9/2007 | Deffenbaugh et al. |
| 2007/0276386 | A1 | 11/2007 | Gerlach et al. |
| 2008/0119895 | A1 | 5/2008 | Manceau |
| 2008/0183218 | A1 | 7/2008 | Mueller et al. |
| 2009/0029320 | A1 | 1/2009 | Auderset et al. |
| 2009/0228049 | A1 | 9/2009 | Park |
| 2009/0254126 | A1 * | 10/2009 | Orbay .................. A61B 17/151 606/282 |
| 2009/0306675 | A1 | 12/2009 | Wong et al. |
| 2009/0312802 | A1 | 12/2009 | DaSilva |
| 2009/0326591 | A1 | 12/2009 | Spencer, Jr. |
| 2010/0318086 | A1 | 12/2010 | Winemaker |
| 2011/0009866 | A1 | 1/2011 | Johnson et al. |
| 2011/0144698 | A1 * | 6/2011 | Buchbinder ........ A61B 17/8071 606/280 |
| 2011/0213376 | A1 * | 9/2011 | Maxson ............... A61B 17/151 606/88 |
| 2011/0245930 | A1 | 10/2011 | Alley et al. |
| 2012/0130434 | A1 | 5/2012 | Stemniski |
| 2012/0130686 | A1 | 5/2012 | Graumann |
| 2013/0018424 | A1 | 1/2013 | Subik |
| 2013/0211463 | A1 | 8/2013 | Mizuno et al. |
| 2013/0226248 | A1 | 8/2013 | Hatch et al. |
| 2013/0245602 | A1 | 9/2013 | Sweeney |
| 2013/0296872 | A1 * | 11/2013 | Davison ............. A61B 17/1635 606/87 |
| 2014/0058466 | A1 | 2/2014 | Keppler et al. |
| 2014/0107781 | A1 | 4/2014 | Bagga et al. |
| 2014/0180341 | A1 | 6/2014 | Kang et al. |
| 2014/0336658 | A1 * | 11/2014 | Luna .................. A61B 17/1739 606/87 |
| 2015/0032168 | A1 | 1/2015 | Orsak et al. |
| 2015/0045837 | A1 | 2/2015 | Parekh et al. |
| 2015/0051650 | A1 | 2/2015 | Verstreken et al. |
| 2015/0051876 | A1 | 2/2015 | Rueber et al. |
| 2015/0057665 | A1 * | 2/2015 | Neal ...................... A61B 17/15 606/87 |
| 2015/0080717 | A1 | 3/2015 | Ferko |
| 2015/0112343 | A1 | 4/2015 | Medoff et al. |
| 2015/0119987 | A1 | 4/2015 | Davignon et al. |
| 2015/0223824 | A1 | 8/2015 | Mebarak |
| 2015/0257899 | A1 * | 9/2015 | Luna .................. A61B 17/1739 623/21.18 |
| 2015/0272598 | A1 * | 10/2015 | Dubois ................ A61B 17/151 606/280 |
| 2015/0305752 | A1 * | 10/2015 | Eash .................... A61B 17/151 606/82 |
| 2015/0366594 | A1 | 12/2015 | Berghs et al. |
| 2016/0022336 | A1 | 1/2016 | Bateman |
| 2016/0030064 | A1 | 2/2016 | Dacosta et al. |
| 2016/0038186 | A1 | 2/2016 | Herzog et al. |
| 2016/0051298 | A1 | 2/2016 | Malinin |
| 2016/0235445 | A1 | 8/2016 | Katrana et al. |
| 2016/0287335 | A1 * | 10/2016 | Goto ...................... A61B 17/80 |

(56) References Cited

U.S. PATENT DOCUMENTS

| | | |
|---|---|---|
| 2017/0027628 A1 | 2/2017 | Kim et al. |
| 2017/0119405 A1 | 5/2017 | Triplett et al. |
| 2018/0289380 A1 | 10/2018 | Mauldin et al. |

OTHER PUBLICATIONS

Dobbe, et al., "Patient-Tailored Plate for Bone Fixation and Accurate 3D Positioning in Corrective Osteotomy", vol. 51, No. 1-2, Medical & Biological Engineering & Computing, Feb. 2013, pp. 19-27.
Extended European Search Report and Written Opinion for EP Application No. 18165822.0, dated Sep. 5, 2018.
Partial European Search Report and Written Opinion for EP Application No. 18178063.6, dated Nov. 19, 2018.

* cited by examiner

PLATE SELECTION USER INTERFACE AND DESIGN TOOL WITH DATABASE

CROSS-REFERENCE TO RELATED APPLICATIONS

This application claims the benefit of the filing date of U.S. Provisional Patent Application No. 62/482,422 filed Apr. 6, 2017, the disclosure of which is hereby incorporated herein by reference.

TECHNICAL FIELD

The present disclosure generally relates to orthopedic surgeries involving bone plating systems and methods of bone plate fixation. Particularly, disclosed herein is a patient-specific plating system that may include a best-fit bone plate, a semi-customized bone plate, or a fully-customized bone plate, in addition to methods of creating and using said bone plates.

BACKGROUND OF THE INVENTION

Bone plating systems are often used to correct bone deformities resulting from trauma or degenerative conditions. For example, surgeons use bone plating systems to set or stabilize bone portions in cases involving fractures, osteotomies, or other deformity conditions.

In many applications, a bone plate is used to hold one or more bone portions in a corrected position for healing. Some surgeons may choose to use a standard bone plate that could sufficiently hold the one or more bone portions in the corrected position for healing, for example, within a predefined confidence interval. Use of a standard bone plate can shorten the duration and difficulty of the correction procedure. A standard bone plate also may be cheaper and easier to manufacture, compared to a semi- or fully-customized bone plate. Because of these advantages, there is a need for a simple method of selecting a standard bone plate that best fits a patient's bone anatomy. However, a bone plate of standard size and shape may be undesirable for a few reasons.

As one example, a standard bone plate may not fit special situations or complex anatomy. This is especially relevant for patients with Charcot, midfoot, and ankle deformities.

Also, a standard bone plate may cause pain and discomfort for a patient. This may occur when a bone-contacting surface of a standard bone plate does not correspond well with a patient's bone anatomy.

Further, a standard bone plate may negatively impact the healing process. In some cases, the location and number of screw holes on the standard bone plate is not sufficient for proper plate fixation. For example, if the location of a screw hole corresponds to a weak bone area in a patient with osteoporosis, then the bone plate may not be properly secured and the one or more bone portions may not be properly aligned.

Thus, there remains a need for bone plating systems that can be semi- or fully-customized for specific patients in order to treat special situations or complex anatomy, reduce pain and discomfort, and/or promote the healing process.

Additionally, in certain cases, a surgeon may need to make a bone cut in order to arrange the one or more bone portions in the corrected position for healing. Often, a surgeon may need to perform bone cuts at multiple angles, which can be difficult for special situations or complex anatomy. Therefore, it would be desirable for a bone plating system to include a complementary cut guide to direct bone cuts which may be required to properly position the one or more bone portions in the corrected position.

SUMMARY OF THE INVENTION

A first aspect of the present invention is a bone plate for correcting a deformity in first and second bone portions having a deformed position with respect to each other. The bone plate may include a body having first and second sections and superior and inferior surfaces, wherein the inferior surface having a preoperatively planned shape to match an outer surface of each of the first and second bone portions when the first and second bone portions are in a corrected position different than the deformed position, and wherein the inferior surface of the first section is adapted to contact the outer surface of the first bone portion above an apex point of the deformity and the inferior surface of the second section is adapted to contact the outer surface of the second bone portion below the apex point of the deformity when the first and second bone portions are in the corrected position.

In accordance with other embodiments of the first aspect, the body may define a profile wherein the profile is preoperatively planned to match the outer surfaces of the first and second bone portions in the corrected position. Moreover, a thickness of the body may define a linear distance between the superior and inferior surfaces. In some embodiments, the thickness may vary from a first end adjacent the first section to a second end adjacent the second section.

In certain applications, the bone plate may also include at least one fixation hole in each of the first and second sections of the body and the location of the fixation holes may correspond to areas of the first and second bone portions having higher relative density. Accordingly, in some embodiments, the bone plate may further comprise a first fixation element insertable into the first fixation hole in the first section and a second fixation element insertable into the second fixation hole in the second section. Further, the fixation hole may be adapted to receive a fixation element at a plurality of angles. For example, in some embodiments, one of the fixation holes may be larger than another one of the fixation holes such that a fixation element in the one fixation hole is able to change angles during insertion. Also, the first and second fixation elements may be different lengths.

A second aspect of the present invention is also a bone plate for correcting a deformity in first and second bone portions having a deformed position with respect to each other. In the second aspect, the bone plate may include a body having first and second sections and superior and inferior surfaces, the inferior surface having a preoperatively planned shape to match an outer surface of each of the first and second bone portions when the first and second bone portions are in a corrected position different than the deformed position, the body also having at least one fixation hole adapted to contact an area of the first or second bone portions having higher relative density.

A third aspect of the present invention is a system for correcting a deformity in first and second bone portions having a deformed position with respect to each other. The system may include a cut guide fixable to each of the first and second bone portions in a deformed position, the cut guide having at least one cutting slot for resecting a bone cut out from at least one of the first and second bone portions. The system may also include a bone plate having first and second sections and superior and inferior surfaces, the inferior surface having a preoperatively planned shape to match an outer surface of each of the first and second bone portions when the first and second bone portions are in a corrected position different than the deformed position. The system may further include at least two fixation elements for fixing the bone plate to the first and second bone portions in the corrected position.

A fourth aspect of the present invention is a method for generating a corrected bone model. The method may include calculating an apex point of a deformity in first and second bone portions, the first and second bone portions having a deformed position with respect to each other; defining an axis of rotation about the apex point; and rotating the second bone portion along the axis of rotation until the first and second bone portions are in a corrected position different from the deformed position.

In accordance with other embodiments of the fourth aspect, the method may also include defining an osteotomy plane based on an apex point. The method may further include calculating the area of a gap between the first and second bone portions in the corrected position.

A fifth aspect of the present invention is a method for designing a bone plate for correcting a deformity in first and second bone portions having a deformed position with respect to each other. The method may include evaluating relative bone densities of the first and second bone portions; defining a profile of a body of the bone plate according to a corrected bone model, wherein first and second bone portions are in a corrected position different from the deformed position; defining an inferior surface of the body of the bone plate according to the corrected bone model; and defining a location of at least one fixation hole in the body of the bone plate based on the evaluation of relative bone densities, wherein the location of the at least one fixation hole corresponds to an area having higher relative density.

In accordance with other embodiments of the fifth aspect, the method may also include determining the total number of fixation holes in the body of the bone plate based on the evaluation of relative bone densities. The method may further include varying a thickness of the body of the bone plate from a first end adjacent a first section of the bone plate to a second end adjacent a section of the bone plate according to the corrected bone model, wherein the thickness of the body is defined by a linear distance between superior and inferior surfaces of the body. In some embodiments, the step of defining a profile of the body of the bone plate includes customizing the profile to match an outer surface of each of the first and second bone portions in the corrected position. In other embodiments, the step of defining a location of at least one fixation hole includes enforcing boundaries corresponding to minimum and maximum plate dimensions.

In certain applications, the method may additionally include generating a cut guide to direct bone cut outs or generating a drill guide to direct insertion of fixation elements at a pre-specified drill hole angle. In some embodiments, the step of generating a drill guide includes calculating a desired length of a fixation element.

Also, in certain applications, the step of evaluating relative bone densities is based on comparative analysis between scan slices of a bone sample and scan slices of the first and second bone portions. In certain other embodiments, the step of evaluating relative bone densities is based on comparative analysis between scan slices of the first and second bone portions.

Moreover, in some embodiments of the method, it may also include determining the size of at least one fixation hole according to the corrected bone model such that a fixation element can pivot during actuation.

A sixth aspect of the present invention is a method for correcting a deformity in first and second bone portions having a deformed position with respect to each other. The method may include calculating an apex point of the deformity; positioning a bone plate having first and second sections and superior and inferior surfaces, the inferior surface having a preoperatively planned shape to match an outer surface of each of the first and second bone portions when the first and second bone portions are in a corrected position different than the deformed position; securing the first section of the bone plate to the first bone portion with a first fixation element; and rotating the second bone portion about the apex point until the bone is in the corrected position.

In accordance with other embodiments of the sixth aspect, the method may also include securing the second section of the bone plate to the second bone portion with a second fixation element. Moreover, in some embodiments, an inferior surface of the first section is adapted to contact the outer surface of the first bone portion above an apex point of the deformity and an inferior surface of the second section is adapted to contact the outer surface of the second bone portion below the apex point of the deformity when the first and second bone portions are in the corrected position.

In certain applications, the rotating step of the method includes inserting a second fixation element through a fixation hole in the second section of the bone plate and into at least a part of the second bone portion; and actuating the second fixation element. The method may also include placing a bone graft in a gap between the first and second bone portions in the corrected position. Furthermore, the method may include using a cut guide to direct bone cut outs or using a drill guide to direct insertion of fixation elements at a pre-specified drill hole angle. Even further, the method may also include performing an osteotomy at the apex point of the deformity.

A seventh aspect of the present invention is a cut guide for directing a cut in a bone. The cut guide may include a body having superior and inferior surfaces and upper and lower sections, the inferior surface having a preoperatively planned shape to match an outer surface of the bone, the body also having at least one cutting slot extending from the superior surface through to the inferior surface, wherein the bone has proximal and distal surfaces and two opposing medial sides, and wherein the upper section of the body is adapted to contact the proximal surface of the bone and the lower section of the body is adapted to contact a medial side of the bone.

In accordance with other embodiments of the seventh aspect, the cut guide may also include at least one pin, wherein the body includes at least one aperture adapted to receive the at least one pin. In some embodiments, the at least one cutting slot of the cut guide corresponds to a closing wedge osteotomy. In some other embodiments, the at least one cutting slot corresponds to an opening wedge osteotomy.

An eighth aspect of the present invention is a method for selecting a bone plate for correcting a deformity in first and second bone portions having a deformed position with respect to each other. The method may include identifying a landmark location on a corrected bone model, wherein first and second bone portions are in a corrected position different from the deformed position. It may also include accessing a library of prefabricated bone plate designs and comparing a landmark location to a fixation hole location on each of the prefabricated bone plate designs in the library. The method may further include determining which prefabricated bone plate design best fits the corrected bone model based on an average proximity of the landmark location and the fixation hole location.

In some embodiments, the landmark locations may correspond to areas of the first and second bone portions having higher relative densities. Moreover, there may be at least landmark locations wherein two are extreme proximal locations and one is an extreme distal location.

In accordance with other embodiments of the eighth aspect, the comparing step may involve showing the landmark locations and at least one cluster of possible fixation hole locations on the corrected bone model, corresponding to possible prefabricated bone plate designs. In certain applications, the method may also include selecting an additional landmark location based on the at least one cluster of possible fixation hole locations. The method may also include changing the location of a landmark and regenerating the at least one cluster of possible fixation hole locations.

Furthermore, in some embodiments of the eighth aspect, the average proximity must be within a predefined tolerance level that would be adequate for healing. Also, the determining step may further involve evaluating the adequacy of the best fit prefabricated bone plate design for healing.

BRIEF DESCRIPTION OF THE DRAWINGS

Various embodiments of the present invention can now be discussed with reference to the appended drawings. It is appreciated that these drawings depict only typical embodiments of the invention and are therefore not to be considered limiting of its scope.

FIG. 17b shows an enlarged view of the plate profile of FIG. 17a.

DETAILED DESCRIPTION OF THE INVENTION

Those of skill in the art can recognize that the following description is merely illustrative of the principles of the invention, which may be applied in various ways to provide many different alternative embodiments.

Depending on the application, a surgeon may choose to use a customized bone plate or a prefabricated bone plate. The following paragraphs will describe the creation and use of a fully-customized patient specific bone plate. A fully-customized bone plate may provide better deformity correction, for example, when treating special situations or complex anatomy. A fully-customized bone plate having a preoperatively planned shape to match the outer surface of the patient's bone anatomy may also reduce pain and discomfort and/or promote the healing process. It also can help the surgeon ensure proper plate alignment and fixation during the surgery.

Figure 1:
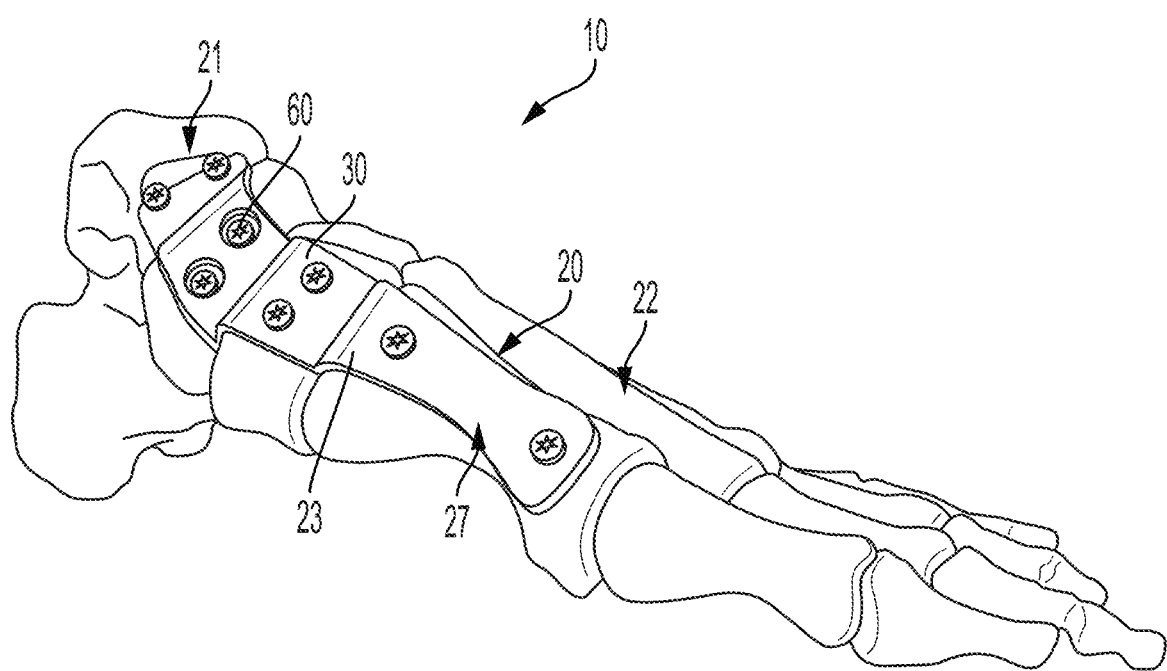
FIG. 1 is a perspective view of a patient-specific plating system according to one embodiment.

FIG. 1 shows a patient-specific plating system 10 according to one embodiment of the present invention. System 10 includes a customized bone plate 20 comprising a body 23 having a first section 21 and a second section 22. Body 23 also includes a superior surface 27 and an inferior surface 29 (not shown). Inferior surface 29 is a bone-contacting surface. As shown, body 23 further includes fixation holes 30 adapted to receive fixation elements 60.

Figure 2:
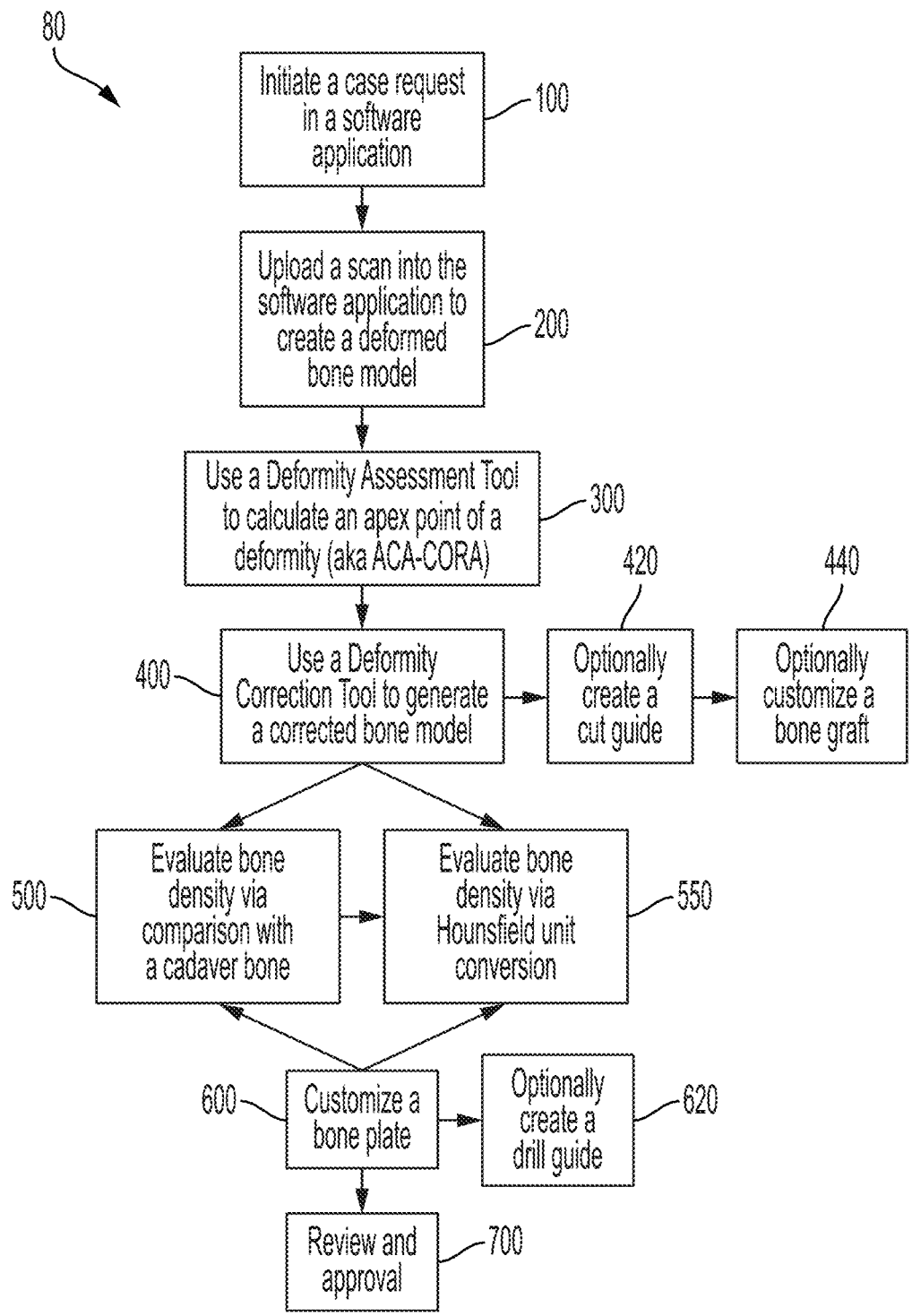
FIG. 2 is a block diagram depicting a pre-operative plan according to one embodiment.

The creation and use of a customized bone plate according to the present invention can involve in-depth pre-operative planning One embodiment of a pre-operative plan 80 is illustrated as a flowchart in FIG. 2.

Many steps of pre-operative plan 80 use a software application. The software application runs as an interactive platform in which a surgeon can design and customize a bone plate for a specific patient. The software application could be web-based or installed by CD.

Computer-implemented methods of generating a data set that geometrically defines a bone plate design are known in the art. For example, U.S. Pat. Pub. No. 2015/0051876, hereby incorporated by reference in its entirety, discloses a technique for generating such a bone plate design.

The first step of pre-operative plan 80 may comprise logging-in to the software application and initiating a case request 100 (FIG. 2). In the preferred embodiment, each surgeon has a unique username and password to reach a profile page. The surgeon's profile page may have a list of patients and associated cases. At this point, the surgeon may optionally modify an existing case or request to initiate a new case.

Figure 3:
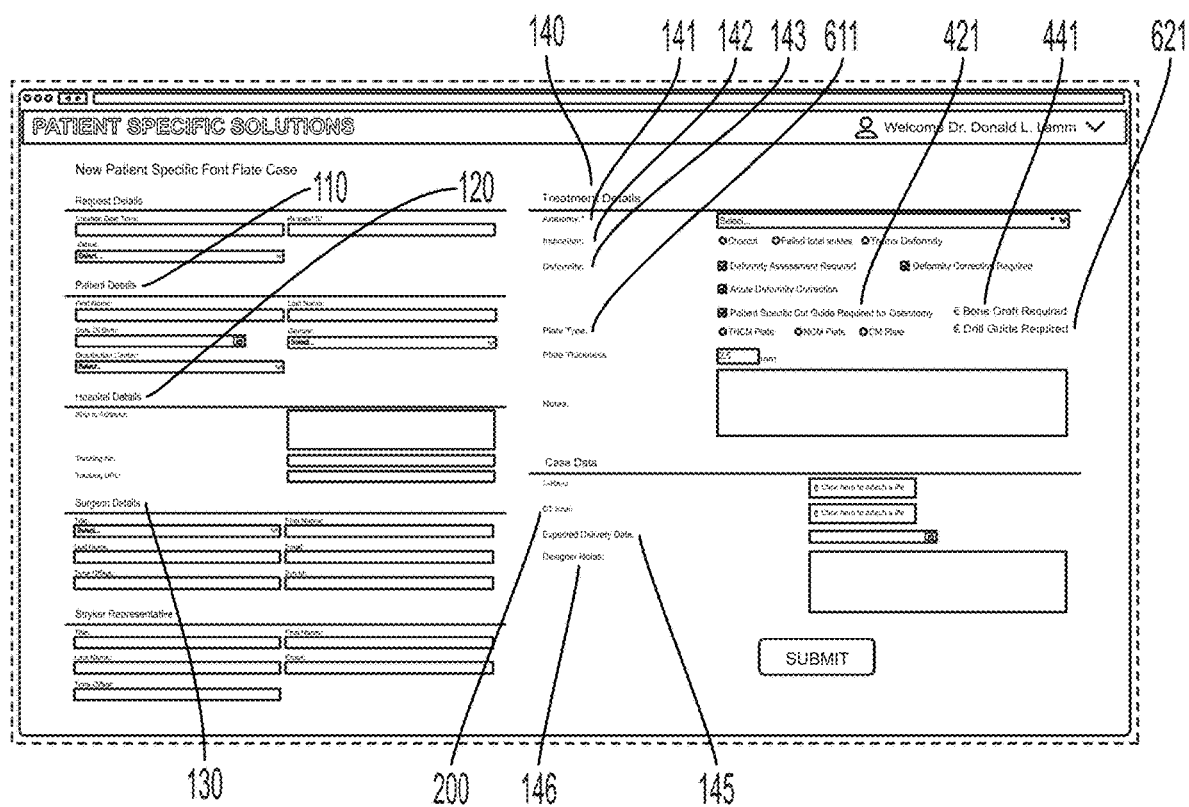
FIG. 3 shows one embodiment of initiating a case request, as part of the pre-operative plan of FIG. 2.

Upon initiating a new case for a patient, the surgeon can enter case details, e.g., patient information 110, hospital information 120, and surgeon information 130, as shown in FIG. 3. The surgeon can also enter treatment information 140 including: anatomy 141; indication 142, e.g., Charcot, midfoot, ankle, etc.; and deformity 143, e.g., assessment required, multiple assessments required, correction required, etc. In addition, the surgeon can select an expected delivery date 145 and enter any other design notes 146. For example, the surgeon may note, "provide additional fixation hole at $2^{nd}$ metatarsal" based on a desired position for healing and/or experience from other similar cases. Moreover, the surgeon may indicate a need for a cut guide 421, a bone graft 441, and/or a drill guide 621, as will be discussed below.

As the next step of pre-operative plan 80, the surgeon can upload a scan of the patient's bone into the software application to create a deformed bone model 200 (FIG. 2). In the deformed bone model, there is a first portion of bone 11 and a second portion of bone 12 which are in a deformed position with respect to each other.

In the preferred embodiment, a computed tomography ("CT") image or magnetic resonance imaging ("MRI") image including 3D data may be used such that the deformed bone model can closely mirror the patient's anatomy. Instead, an X-ray image including 2D data could also be used.

Figure 4:
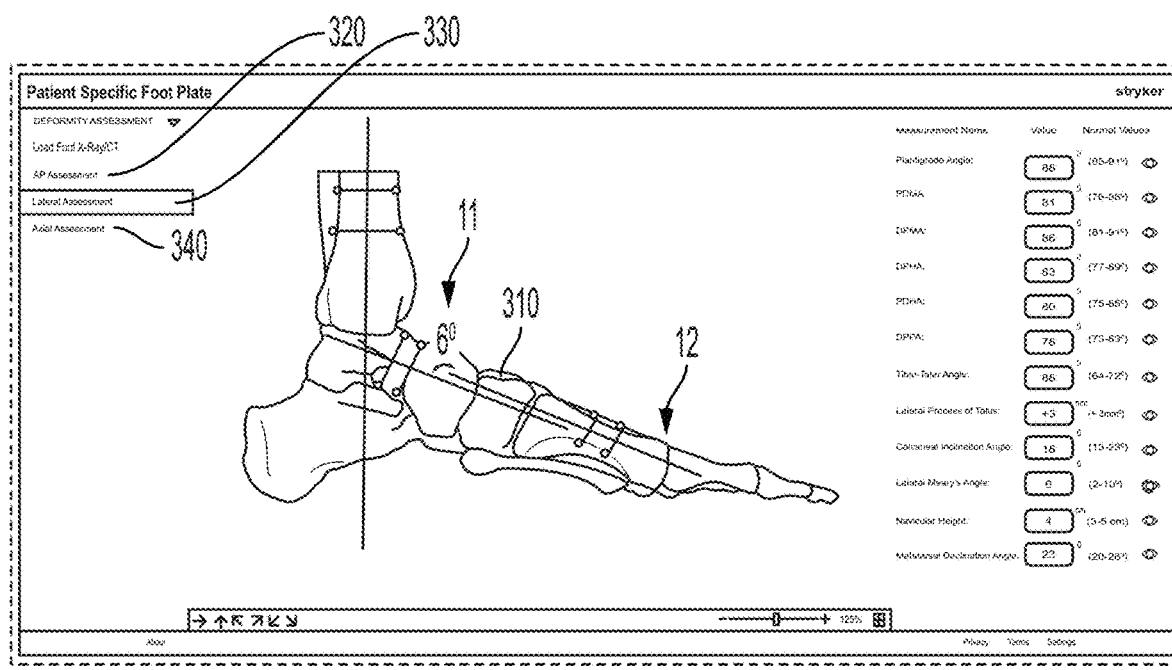
FIG. 4 shows one embodiment of assessing a deformity, as part of the pre-operative plan of FIG. 2.

As another step of pre-operative plan 80, the surgeon may use a 'Deformity Assessment Tool' to calculate an apex point 310 of a deformity, also known as the ACA-CORA to those skilled in the art 300 (FIG. 2). That is, the 'Deformity Assessment Tool' may be used to calculate an axis of correction of angulation ("ACA") and a center of rotation of angulation ("CORA") according to the deformed bone model (FIG. 4). The surgeon may use standard measurement techniques known to those of ordinary skill in the art to calculate apex point 310. For example, *Principles of Deformity Correction*, by Dror Paley, published in 2002 and hereby incorporated by reference in its entirety, discloses many such techniques.

After calculating apex point 310 of the deformity, the surgeon may use a 'Deformity Correction Tool' to generate a corrected bone model 400 (FIG. 2). In the corrected bone model, first and second bone portions 11, 12 are in a corrected position different from the deformed position. As an example, the software application may be used to calculate a Meary's angle of a deformity and simulate a correction procedure in order to generate a corrected bone model for Charcot or Midfoot indications.

Figure 5:
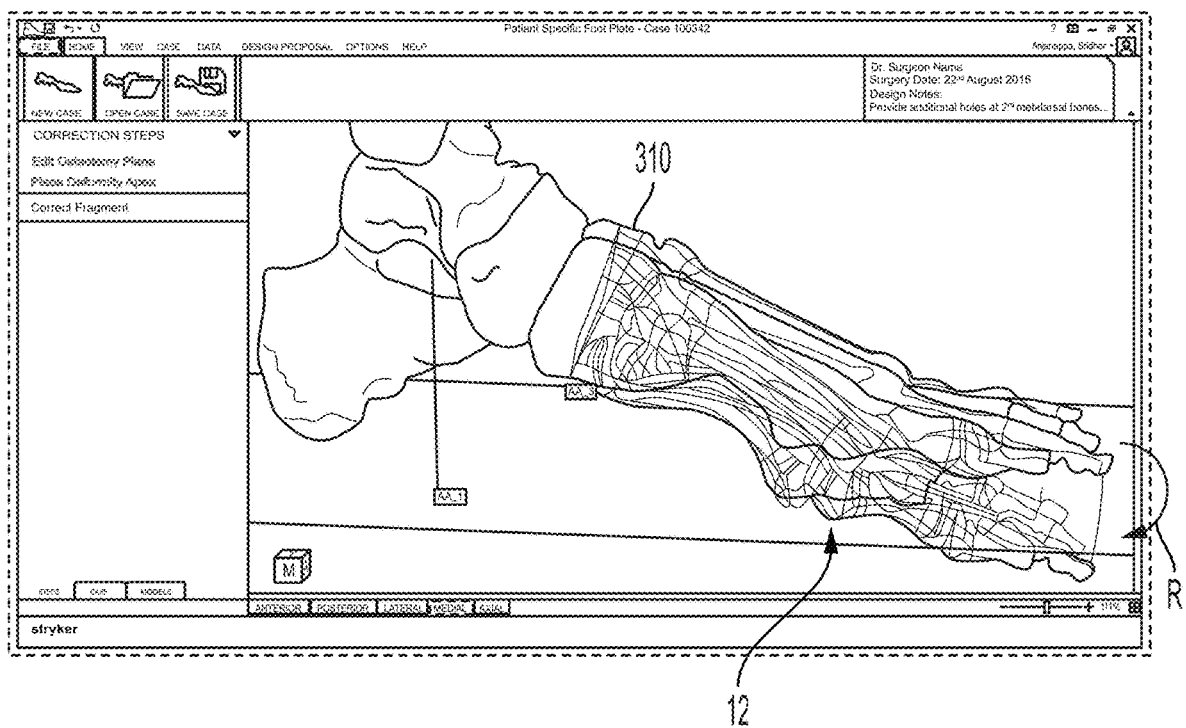
FIG. 5 shows one embodiment of correcting a deformity, as part of the pre-operative plan of FIG. 2.

To generate the corrected bone model, the surgeon can project an axis of rotation R about apex point 310 onto the deformed bone model. Then, the surgeon can visualize deformation correction in real time by dragging and rotating the second bone portion 12 along the axis of rotation R for a certain distance Θ, as will be discussed further below (FIG. 5).

Figure 6:
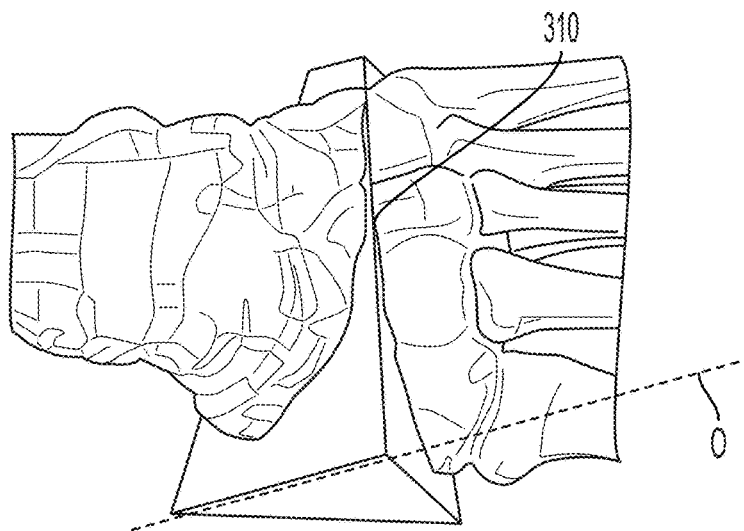
FIG. 6 shows one embodiment of an osteotomy to correct the deformity of FIG. 5.

In certain cases, the surgeon may need to perform an osteotomy in order to correct the deformity. Two common types of osteotomy procedures may be used, i.e., a closing wedge or an opening wedge. A closing wedge may require an inverted "V" cut, e.g., for acute planar correction, or a complex double "V" cut, e.g., for acute two degree correction. A complex double "V" cut may also be known as a "trapezoid" cut to those having ordinary skill in the art. FIG. 6 shows an osteotomy plane O corresponding to a closing wedge osteotomy. An opening wedge generally requires a straight "V" cut, e.g., for acute rotational correction.

Figure 7:
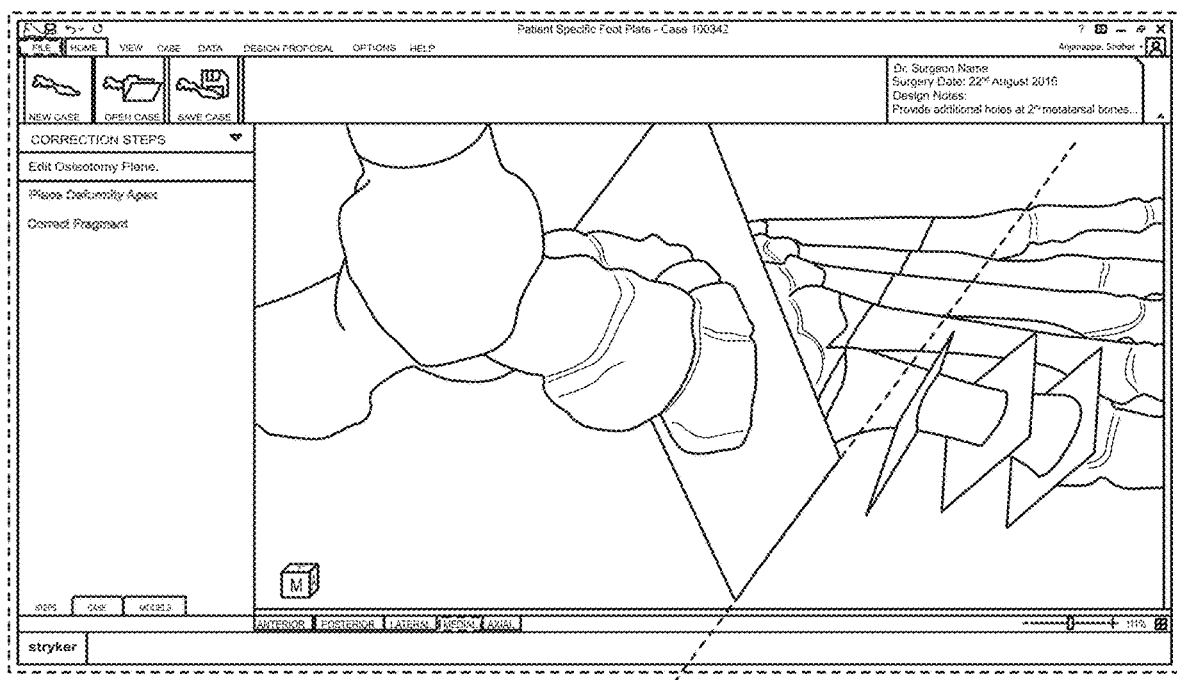
FIG. 7 shows an osteotomy plane according to the osteotomy of FIG. 6.

To visualize the osteotomy, the surgeon may project the osteotomy plane O onto the deformed model, as shown in FIG. 7. In the preferred embodiment, the osteotomy plane O passes through apex point 310. Osteotomy plane O may define a bone cut out 802 that is to be removed, as will be discussed further below. Notably, the surgeon can manipulate osteotomy plane O in the anterior, posterior, lateral, medial, and axial directions as desired. The surgeon can also view the osteotomy plane O in a 2D or 3D plane.

In some cases, the surgeon may require a cut guide for an osteotomy procedure. FIG. 8 shows cut guide 422 for acute planar correction, which corresponds to the closing wedge osteotomy in FIG. 6. Cut guide 422 identifies bone cut out 802 required for proper alignment of first and second bone portions 11, 12 and for proper plate placement (FIG. 8b). When the surgeon is entering treatment information 100, the surgeon has the option to indicate a need for a cut guide 421 (FIG. 3). Thus, the software application can create a complementary cut guide according to the corrected bone model 420 (FIG. 2).

Figure 38:
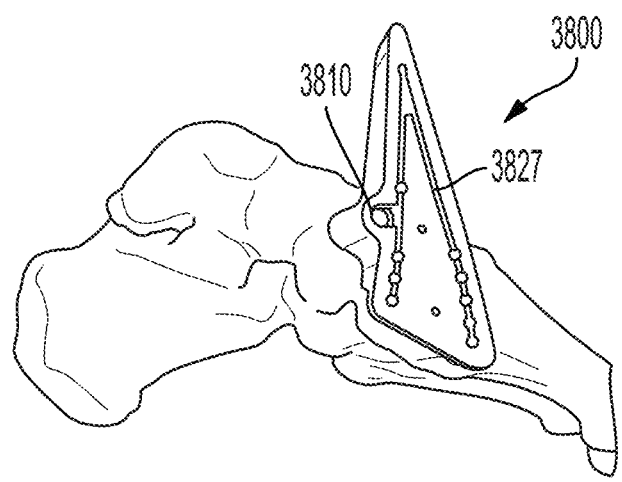
FIGS. 38-40 show different embodiments of cut guides having different cutting slot designs.
Figure 39:
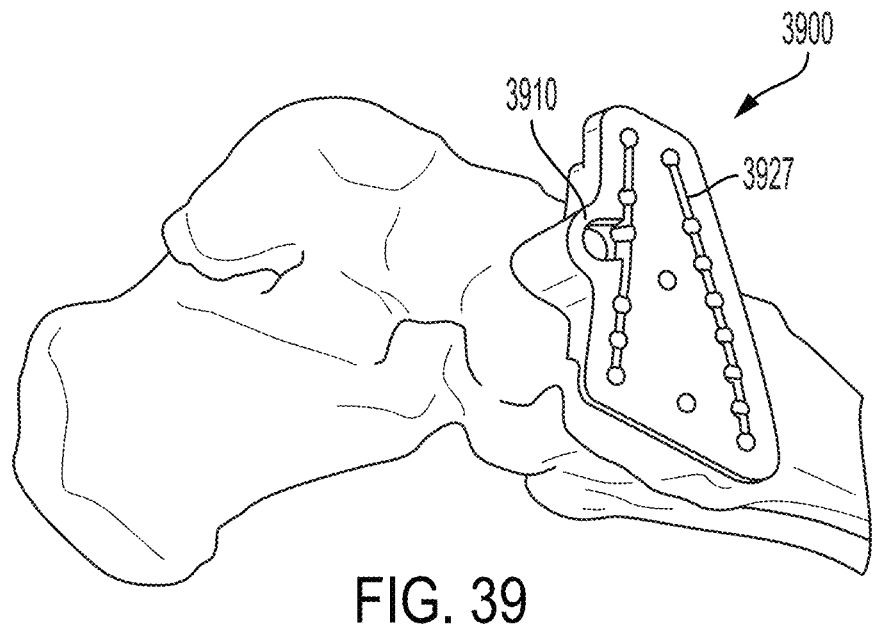
Figure 40:
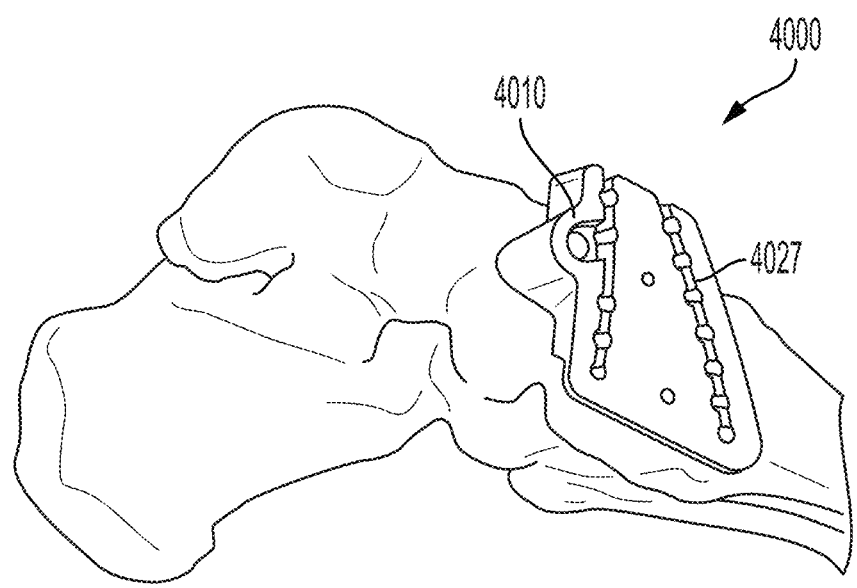

The surgeon may additionally modify the dimensions of the cut guide in real time using the software application. For example, the surgeon may design the cut guide to include another aperture adapted to receive a guiding pin and/or a fixation hole adapted to receive a fixation element. FIG. 38 shows a cut guide 3800 having a fixation hole 3810. The cutting slots 3827 of cut guide 3800 extend up to the axis of rotation. FIG. 39 shows a cut guide 3900 having a fixation hole 3910; however, the cutting slots 3927 are distinct in this "trimmed" embodiment. The surgeon may also design the cut guide depending on the blade type. FIG. 40 shows a cut guide 4000 having a fixation hole 4010. The cutting slots 4027 are open-ended and adapted to receive all blade types.

Figure 8A:
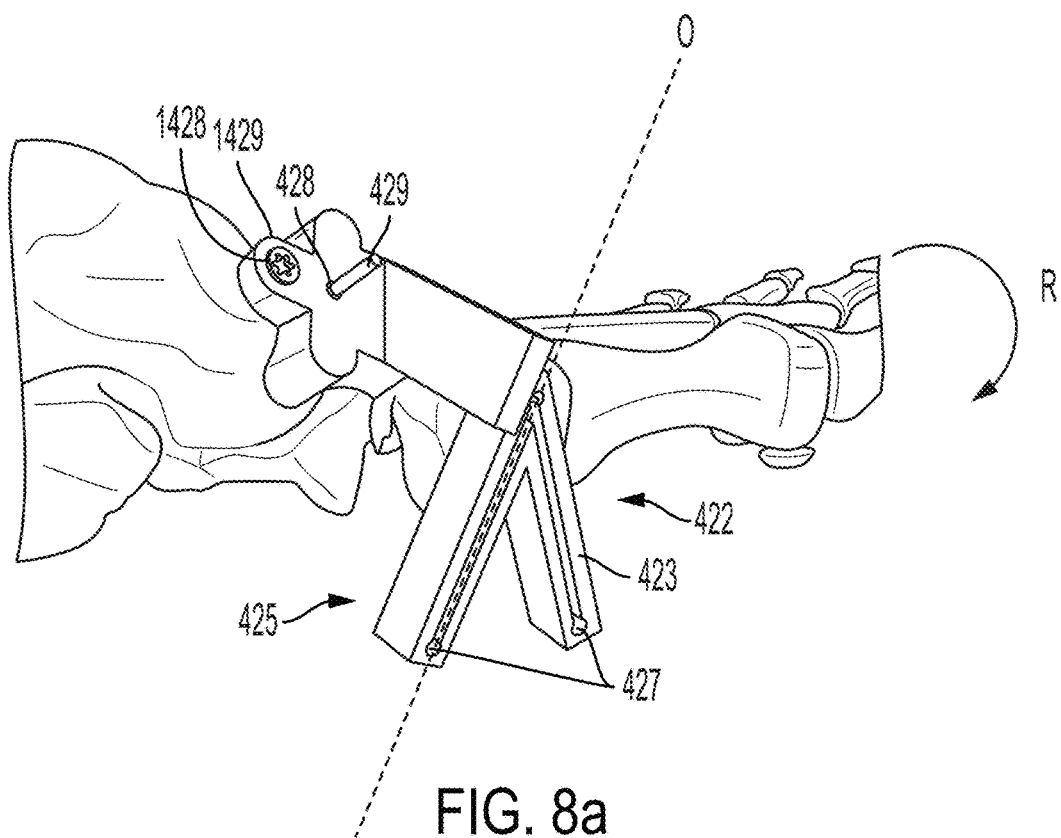
FIGS. 8a and 8b show one embodiment of a cut guide according to the osteotomy of FIG. 6.
Figure 8B:
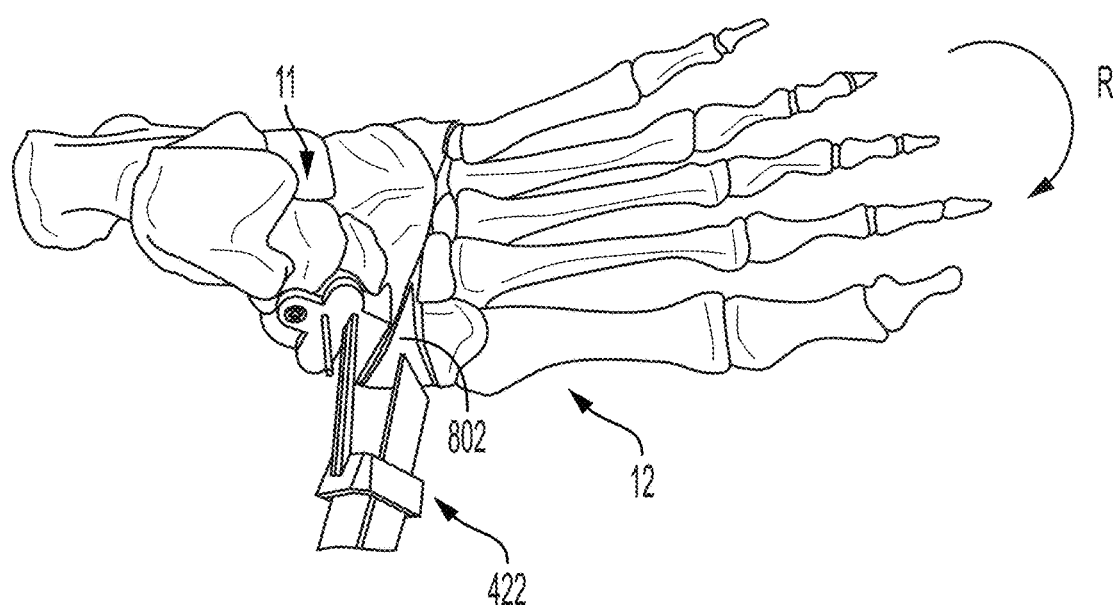

In the embodiment of FIGS. 8a and 8b, cut guide 422 has superior and inferior surfaces 423, 425. Inferior surface 425 may be preoperatively planned to match the patient's bone anatomy in order to help ensure proper placement of cut guide 422. In turn, this may also help a surgeon perform more accurate bone cuts.

As shown in FIGS. 8a and 8b, cut guide 422 also has two angled cutting slots 427 for making a wedge shaped resection, the cutting slots 427 sized to receive an oscillating saw blade or similar cutting tool. In the preferred embodiment, slots 427 do not allow the saw blade to substantially vibrate during the resection procedure. Cut guide 422 may also have an aperture 428 adapted to receive a pin 429. Pin 429 may help properly position the plate during the resection procedure. In some embodiments, cut guide 422 may also include a fixation hole 1428 adapted to receive a fixation element 1429 in order to help maintain the position of cut guide 422 during the resection procedure.

After the resection procedure, the surgeon may desire to perform additional free-hand bone cuts in order to arrange the first and second bone portions 11, 12 in the corrected position. Thus, cut guide 422 may be used to perform a straight cut, closing wedge osteotomy.

Figure 9:
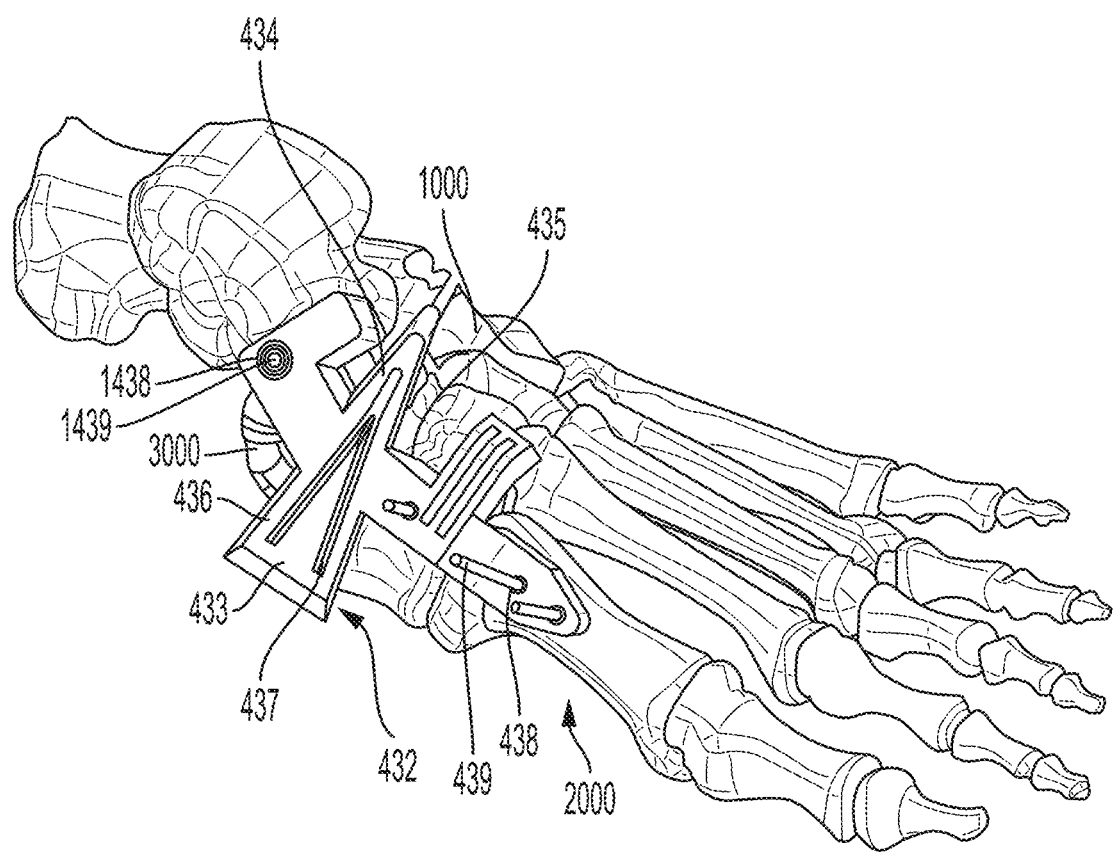
FIG. 9 shows another embodiment of a cut guide according to the osteotomy of FIG. 6.
Figure 10:
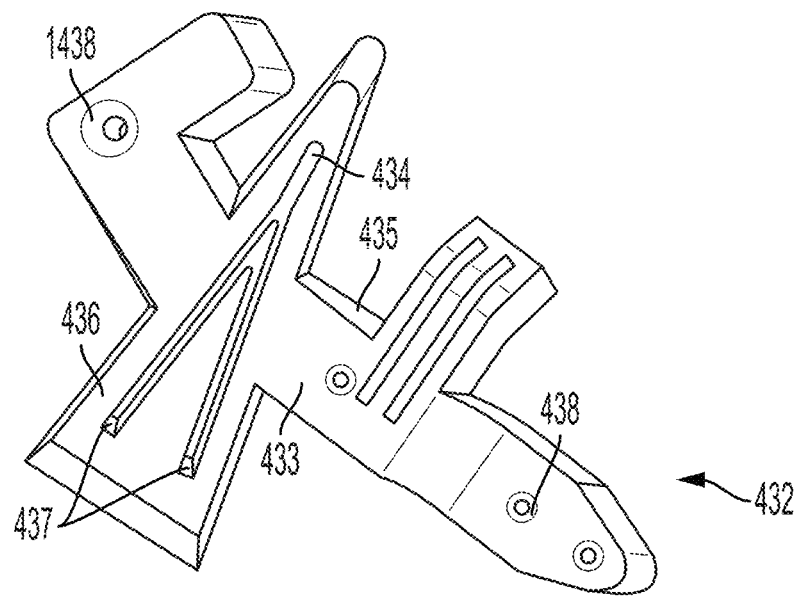
FIG. 10 shows a perspective view of the cut guide of FIG. 9.

FIG. 9 shows an alternative embodiment of a cut guide 432 corresponding to the closing wedge osteotomy in FIG. 6. Cut guide 432 has many similar features that are similarly numbered in comparison with cut guide 422. As such, cut guide 432 has superior and inferior surfaces 433, 435 where inferior surface 435 may also be preoperatively planned to match the patient's bone anatomy. Cut guide 432 also has slots 437 adapted to receive a cutting tool. Further, cut guide 432 includes aperture 438 adapted to receive pin 439 and fixation hole 1438 adapted to receive fixation element 1439.

In certain cases, the surgeon may need to perform multiple bone cuts at multiple angles which can be difficult to perform free hand. To facilitate the resection procedure, cute guide 432 may include upper and lower portions 434, 436. Then, in order to perform accurate multi-angle cuts, the upper portion 434 of cut guide 432 may contact a proximal surface 1000 of a bone, opposite a distal surface 2000; while the lower portion 436 of cut guide 432 may contact one of two opposing medial sides 3000 of the bone. Thus, the surgeon can make multiple multi-angle cuts using a single cut guide. This may be especially useful in cases where a complex double "V" cut is required.

Figure 25:
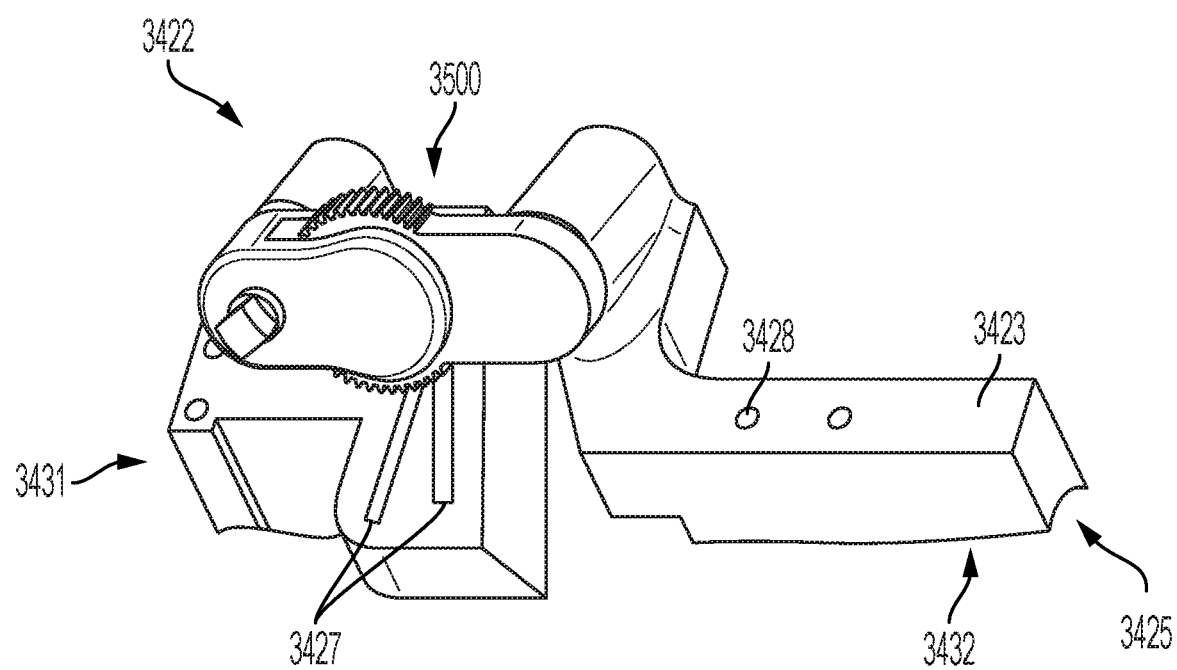
FIG. 25 shows a perspective view of yet another embodiment of a cut guide having first and second guide components coupled together via a joint mechanism.

FIG. 25 shows another embodiment of a cut guide 3422 corresponding to the closing wedge osteotomy in FIG. 6. Cut guide 3422 has many similar features that are similarly numbered in comparison with cut guides 422, 432. Cut guide 3422 has superior and inferior surface 3423, 3425 where inferior surface 3425 may be preoperatively planned to match the patient's bone anatomy. Cut guide 3422 also has slots 3427 adapted to receive a cutting tool as well as apertures 3428 adapted to receive pins 4329 (not shown). Cut guide 3422 may additionally have fixation holes adapted to receive fixation elements as discussed above in relation to different embodiments.

Figure 26:
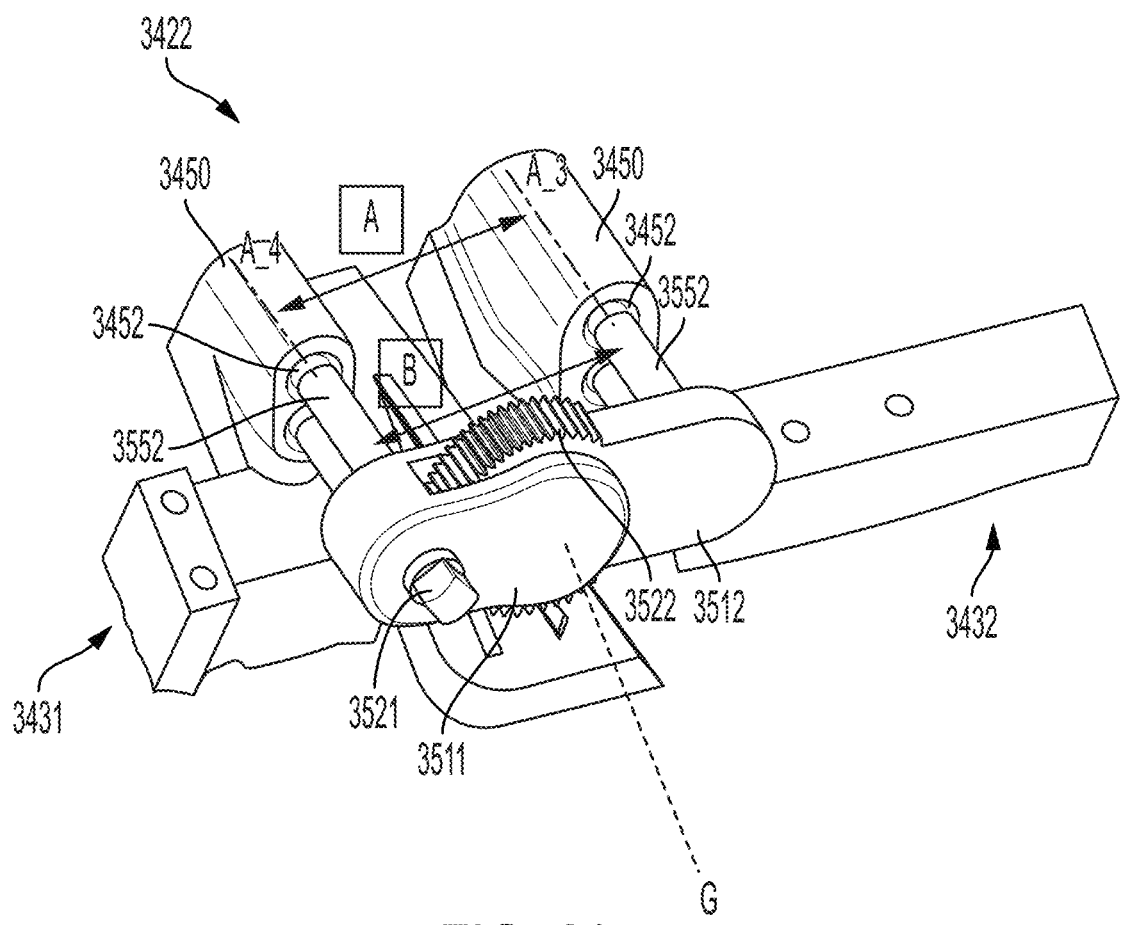
FIG. 26 shows a partially exploded view of the cut guide of FIG. 25.

Cut guide 3422 includes a posterior section 3431 and an anterior section 3432 adapted to contact first and second bone portions 11, 12 respectively. Posterior section 3431 and anterior section 3432 may also be referred to as first and second cut guide components, respectively. As shown more clearly in FIG. 26, the posterior and anterior sections 3431, 3432 are connected by a joint mechanism, i.e. gear module 3500. Each posterior, anterior section 3431, 3432 includes a vertical projection 3450 with at least one peg hole 3452. The distance between peg holes 3452 on posterior and anterior sections 3431, 3432 may be defined by distance A.

Gear module 3500 includes posterior and anterior sections 3511, 3512 which may be aligned with the posterior and anterior sections 3431, 3432 of cut guide 3422. Each section 3511, 3512 of gear module 3500 may further include at least one peg 3552 insertable into the at least one peg hole 3452 in sections 3431, 3432 of cut guide 3422. The distance between the pegs 3552 may be defined by distance B. As such, distances A and B should be equal such that pegs 3552 are insertable into peg holes 3452.

Gear module 3500 may be used after the surgeon makes the desired bone cuts in order to manipulate or rearrange the first and second bone portions 11, 12 from a deformed position into a corrected position. Gear module 3500 may be designed such that anterior section 3512 has an operable end such as a hinged gear head 3522, while posterior section 3511 includes an actuator 3521 configured to operate the hinged gear head 3522. That is, upon actuation of actuator 3521, hinged gear head 3522 will rotate about an axis G causing the distances A,B to decrease and forcing the posterior and anterior sections 3431, 3432 of cut guide 3422 closer together such that first and second bone portions 11,12 may be arranged in the corrected position.

Figure 27:
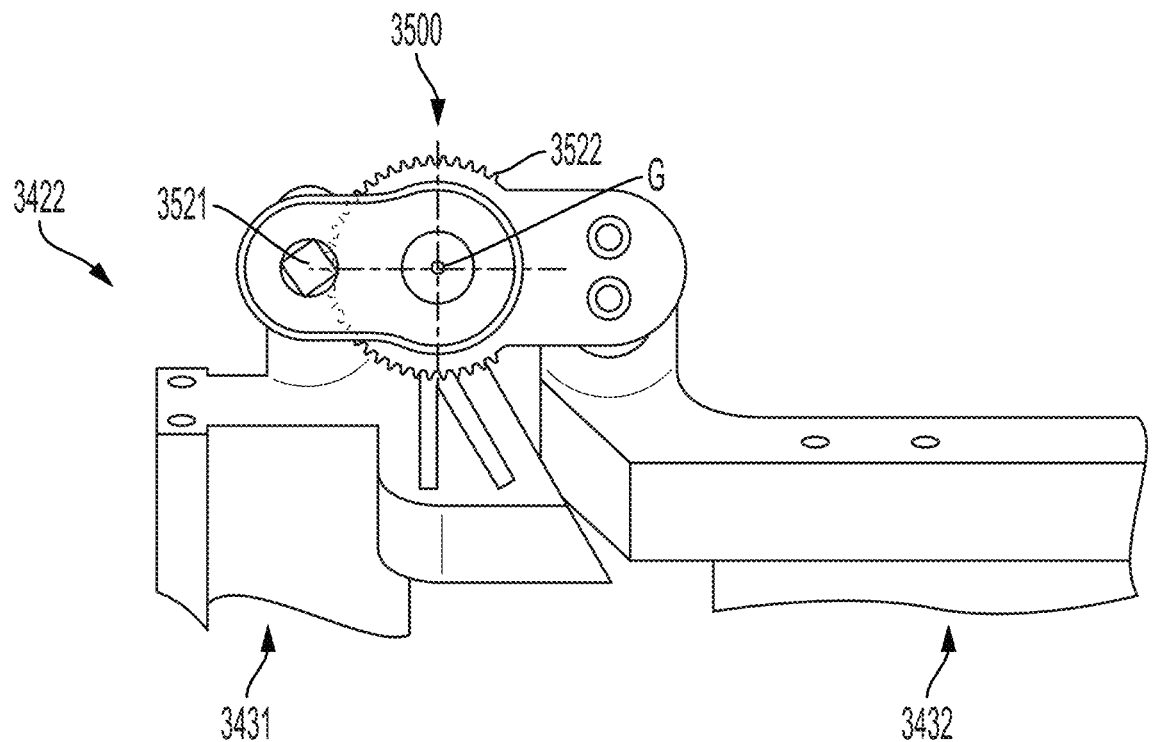
FIG. 27 shows another perspective view of the cut guide of FIG. 25 with a front plane view of the joint mechanism.

FIG. 27 shows an axis of rotation G corresponding to the center of the hinged gear head 3522. When the software application designs cut guide 3422, the position of axis G and the location of pegs 3552 and corresponding peg holes 3452 can be calculated according to the corrected bone model. That is, the software application will align the axis of rotation R and axis G. Accordingly, actuation of the hinged gear head 3522 may cause the anterior section 3512 of gear module 3500 to rotate about axis G and force the anterior section 3432 of cut guide 3422 to move toward the posterior section 3431. As such, actuation of the hinged gear head 3522 may pull the first and second bone portions 11, 12 from the deformed position into the corrected position. In different cases, different embodiments of cut guide 3422 may include more than two pegs 3522 and peg holes 3452. Moreover, the position of axis G and distances A, B may also be different.

It may be useful for a surgeon to use gear module 3500 to restrict motion of the first and second bone portions 11, 12 after the resection procedure has been performed. The hinged design of gear head 3522 can help the doctor ensure the rotation motion is about axis G such that the first and second bone portions 11, 12 may be aligned in the corrected position.

Figure 28:
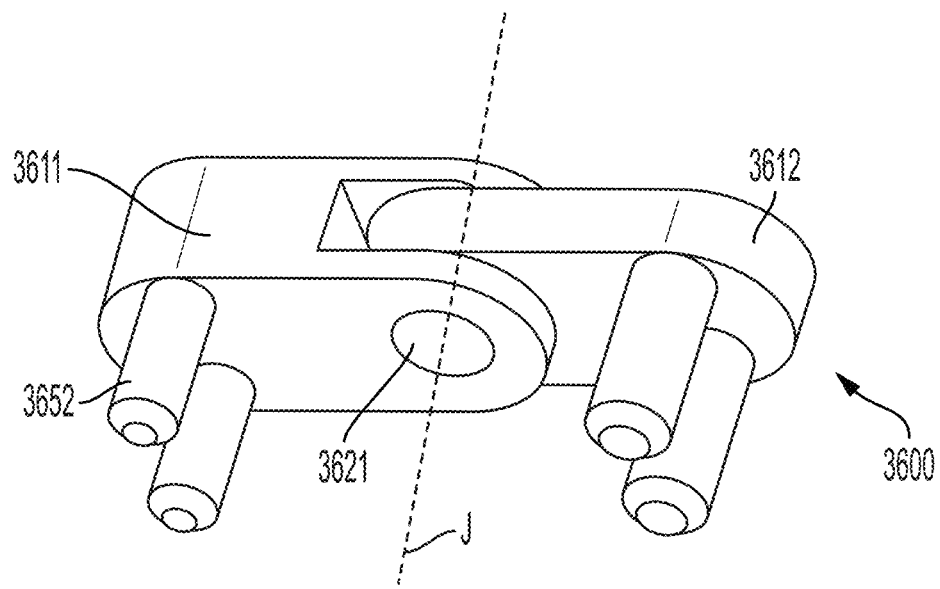
FIG. 28 shows another embodiment of a joint mechanism that can be used to couple first and second guide components.

FIG. 28 shows another embodiment of a joint mechanism, i.e. hinged module 3600, that may connect posterior and anterior sections 3431, 3432 of cut guide 3422. As described above, hinged module 3600 may also be used to rearrange the first and second bone portions 11, 12 from the deformed position into the corrected position. Like gear module 3500, the hinged module 3600 similarly has posterior and anterior sections 3611, 3612 and pegs 3652 insertable into peg holes 3452. Further, an end of the anterior section 3612 may fit within an end of the posterior section 3611 and a pin 3621 may be inserted through both sections 3611, 3612 along an axis of rotation J in order to form a hinged joint. The software application may again be used to calculate the axis J and location of pegs 3652 and corresponding peg holes 3452 according to the corrected bone model. That is, the software application will align the axis of rotation R and axis J. As such, the surgeon may manipulate the anterior section 3611 of module 3600 by hand to rotate the anterior section 3432 of the cut guide toward the posterior section 3431 about axis J. Thus, the surgeon may manually arrange the first and second bone portions 11, 12 in the corrected position.

In an alternative embodiment of hinged module 3600, a ball-joint module may be used. Like the other joint mechanisms 3500, 3600, the ball-joint module may have pre-operatively planned posterior and anterior sections with pegs insertable into peg holes 3452. Moreover, an end of the anterior section may be a sphere that fits within a cavity in an end of the posterior section, thereby forming a ball-joint. Insertion of the pegs into peg holes 3452 will restrict polyaxial motion of the ball-joint such that the anterior section of the ball-joint module can only rotate along a single ball-joint axis. The software will design the location of pegs and corresponding peg holes 3452 according to the corrected bone model, such that the ball-joint axis is aligned with the axis of rotation R. Accordingly, the surgeon may manipulate the anterior section of the ball-joint module by hand to arrange the first and second bone portions 11, 12 in the corrected position.

Figure 11:
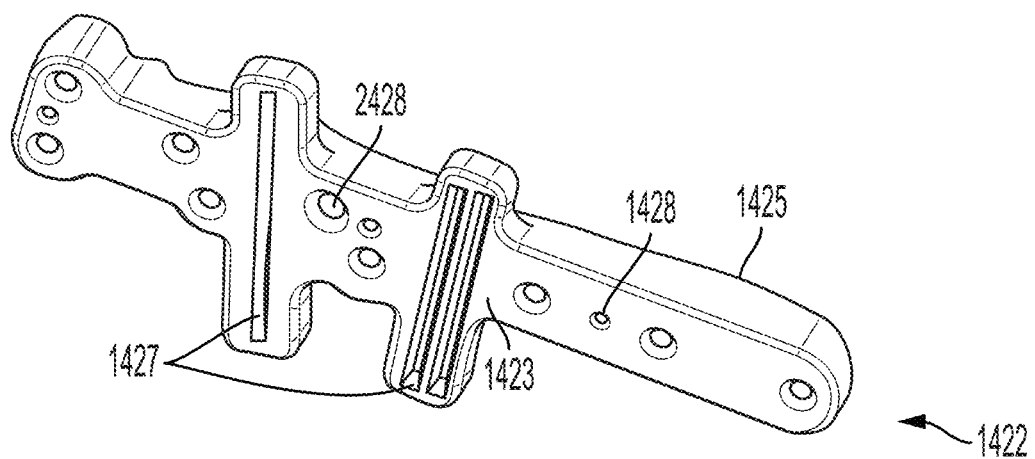
FIG. 11 shows one embodiment of a cut guide according to an osteotomy to correct a different deformity.

As an alternative to the closing wedge osteotomy of FIG. 6, a cut guide 1422 as shown in FIG. 11 may be used to perform an opening wedge osteotomy for certain other cases. Cut guide 1422 has many similar features that are similarly numbered in comparison with cut guides 422,432. Accordingly, cut guide 1422 has superior and inferior surfaces 1423, 1425; slots 1427; and aperture 1428 adapted to receive pin 1429 (not shown). Additionally, cut guide 1422 has at least one fixation hole 2428 adapted to receive fixation element 2429 (not shown).

Cut guide 1422 may optionally be designed to include posterior and anterior sections like cut guide 3422, as well as a hinged module similar to gear module 3500 or ball-joint module 3600 that would force the posterior and anterior sections of the cut guide closer together in order to arrange the first and second bone portions 11, 12 in the corrected position.

Figure 23:
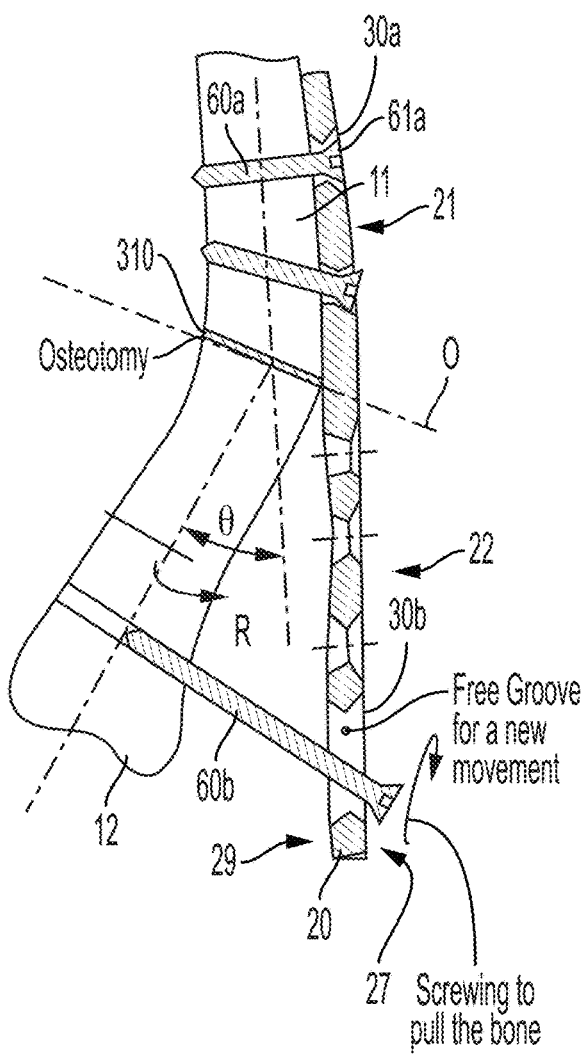
FIG. 23 shows one embodiment of visualizing a patient-specific plating system on a corrected bone model, as part of the pre-operative plan of FIG. 2

Often, the corrected bone model may show a gap 803 between first and second bone portions 11, 12. In some cases, it is desirable to leave gap 803 to allow for bone regrowth. In other cases, the surgeon may require a bone graft 442 to fill gap 803 (FIG. 23). When the surgeon is entering treatment information 100, the surgeon has the option to indicate a need for a bone graft 441 (FIG. 3). Thus, the software application can calculate the area of a bone graft according to the corrected bone model 440 (FIG. 2). The software application can also provide recommendations for ordering bone substitutes. For example, allograft material, polyetheretherketone, stainless steel, or titanium could be used.

In some embodiments, a surgeon may use scan data from a patient's contralateral bone across the sagittal plane to generate the corrected bone model. In those cases, the surgeon may not need to create a deformed bone model 200 or use the Deformity Assessment Tool 300,350 (FIG. 2). Still, the surgeon can design a patient-specific plating system.

In other embodiments, it is possible for a surgeon to use scan data from a database with a library of patient scans for creating the corrected bone model. The database may further include a library of corresponding bone plate designs for the patient scans. Those bone plate designs may be used as a template and further customized for a patient-specific plating system.

In certain cases, a generic corrected bone model may be configured to fit what may be referred to as a 5% female and a 95% male such that it may be used for almost any patient. These generic models may also be gender-specific or age-specific.

As yet another step of pre-operative plan 80, the surgeon may evaluate bone density. As one option, this can be done by performing comparative analysis between scan slices of a bone sample and the same bone in the patient 500 (FIG. 2). The scan of the bone sample may be obtained from a database with a library of patient scans.

Using the software application, the surgeon may perform segmentation analysis on a scan of the bone sample and a scan of the patient's bone to create scan slices. For example, the scan slice may have a thickness of 1 mm similar to X-ray images, but with more detail. Then, the software application can use an algorithm to compare the scan slices of the bone sample with the scan slices of the patient's bone.

The same algorithm may be used to distinguish and segregate each scan slice of the patient's bone with higher density, about the same density, or lower density as compared to the scan slice of the bone sample. Each of the scan slices of the patient's bone may be assigned a color on the RGB color scale to indicate areas of relatively high, moderate, or low density compared to the bone sample. After, the colored scan slices may be combined to show bone volume. The 3D color scheme may then be applied to the corrected bone model and create a color map for the surgeon to evaluate bone density.

Figure 12:
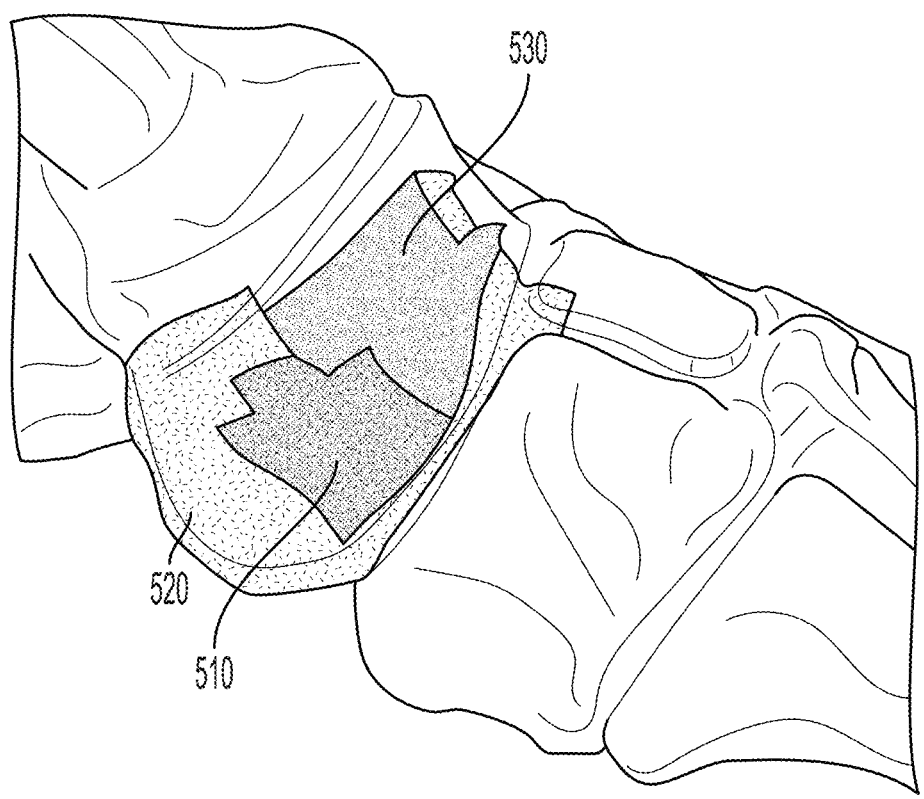
FIG. 12 shows one embodiment of evaluating bone density, as part of the pre-operative plan of FIG. 2

Thus, the software application can provide the surgeon with visual information to evaluate bone density. As FIG. 12 shows, the surgeon can visualize the relative bone densities, where dark grey represents a relatively high density bone area (510), grey represents a relatively moderate density bone area (520), and light grey represents a relatively low density bone area (530). It is possible to use various colors instead of grey scale.

As another option for evaluating bone density, the surgeon can use Hounsfield unit conversion to compare scan slices of the patient's bone to each other 550 (FIG. 2).

Using the software application, the surgeon can perform segmentation analysis on the scan of the patient's bone to create scan slices. Again, the scan slices may have a thickness of 1 mm. Then, the software application can calculate the bone density of each scan slice using Hounsfield values. U.S. Pat. Pub. Nos. 2015/0119987 and 2015/0080717, hereby incorporated by reference in their entirety, disclose methods of deriving bone density from scan data using Hounsfield values.

After, the software application can use an algorithm to assign each scan slice a color on the RGB color scale to indicate areas of higher, about the same, or lower density as compared to each other. For example, green slices are more dense than yellow slices which are more dense than red slices. It is also possible to use a gray scale instead of a RGB color scale. Then, the colored scan slices may be combined to show bone volume and the 3D color scheme may be applied to the corrected bone model, as earlier discussed.

Visual information showing relative bone densities can be very useful to a surgeon when he is deciding which areas of the bone can provide for proper alignment and fixation of a bone plate. In the preferred embodiment, the surgeon can use color filtration options to show only relatively high, moderate, or low density bone areas. This is especially useful for patients with osteoporosis. Accordingly, the surgeon can ensure that fixation holes in a bone plate correspond to bone areas with relatively high or moderate density. It is not usually recommended to drill into areas of bone with relatively low density.

For the next step of pre-operative plan 80, the surgeon can customize the bone plate 600 (FIG. 2). For example, the surgeon may customize the number and location of fixation holes in the bone plate to correspond to areas of bone with relatively high or moderate density.

Figure 13:
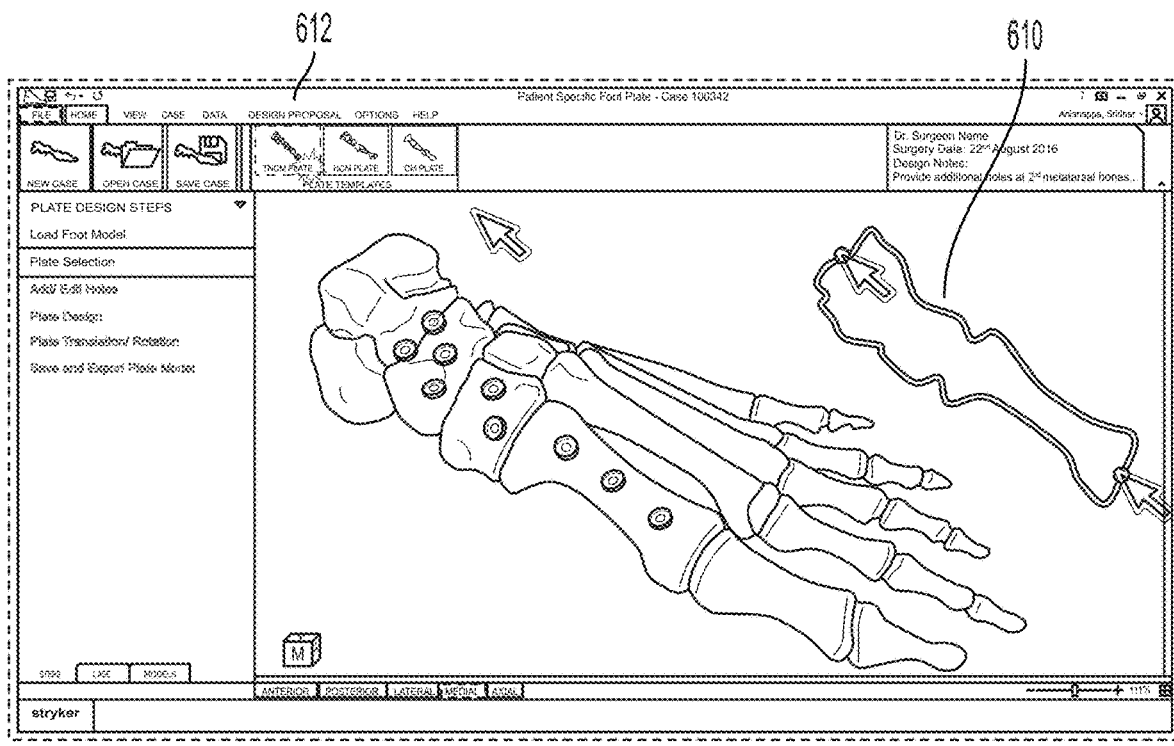
FIG. 13 shows one embodiment of projecting a plate profile over a corrected bone model, as part of the pre-operative plan of FIG. 2

To do so, the surgeon can use the software application to project a plate template over the corrected bone model. The plate template may be a Talus Navicular Cuneiform and Metatarsal (TNCM) plate, a Navicular Cuneiform and Metatarsal (NCM) plate, a Cuneiform and Metatarsal (CM) plate. These templates correspond to standard sized bone plates used for Charcot, midfoot, flat feet, *cavus* foot, and related indications or deformities. As an example, FIG. 13 shows a profile 610 of a TNCM plate template projected over the corrected bone model. When the surgeon is entering treatment information 100, the surgeon has the option to choose which plate type may be used 611 (FIG. 3). The surgeon can change plate types as desired in the options menu 612 (FIG. 13).

Figure 14:
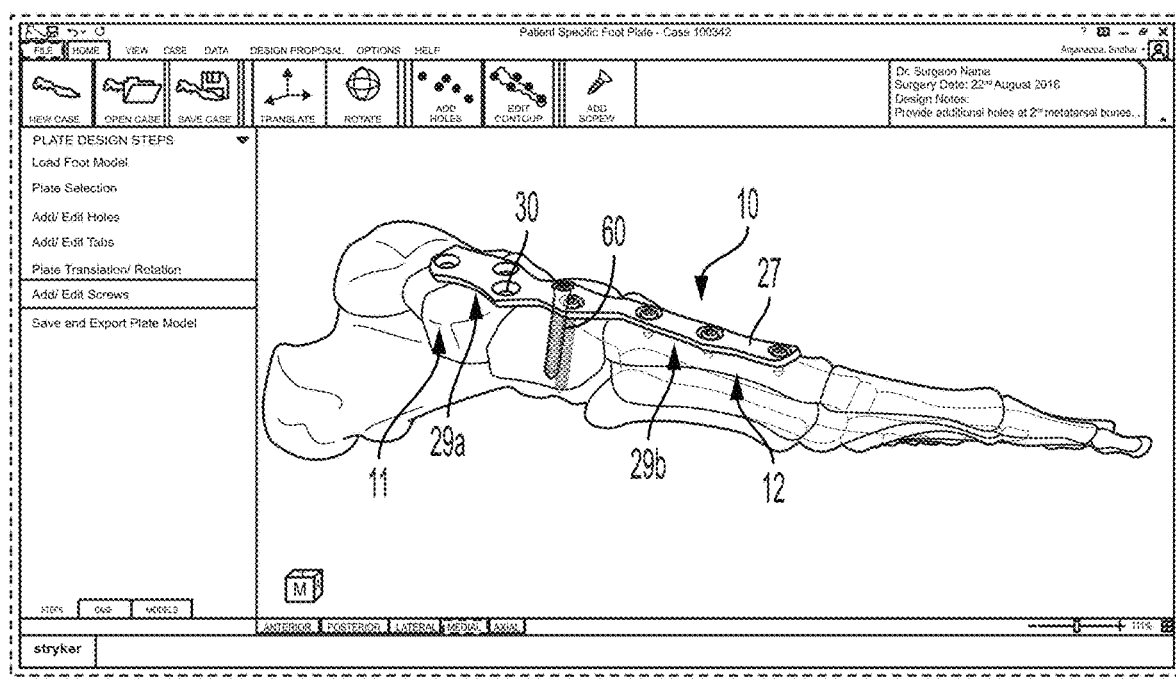
FIG. 14 shows one embodiment of visualizing a screw trajectory through a corrected bone model, as part of the pre-operative plan of FIG. 2

Thereafter, the surgeon can select a type and length of fixation element 60. For example, a 3.5 mm VariAx screw may be used for procedures in the forefoot and midfoot. Then, the software application may illustrate the trajectory of fixation element 60 through the bone volume, as shown in FIG. 14. At this point, the surgeon can adjust the orientation of fixation element 60 and make other modifications.

In certain cases, it may be desirable to use fixation elements of different types or lengths. For example, a surgeon may choose to use mono-axial screws for lower density bone areas and poly-axial screws for higher density bone areas.

By default, the software application may show the minimum number of fixation holes 30 for the selected plate template. That is, the software application will pre-determine the minimum size of a fixation hole 30 such that a fixation element can pivot during actuation relative to the rotation of the second bone portion 12 about axis R. Then, the surgeon can easily add or delete a fixation hole 30, or change the location of a fixation hole 30 by clicking or dragging the cursor. However, it is recommended that profile 610 of the bone plate provide sufficient clearance given the number and location of fixation holes 30.

Figure 15:
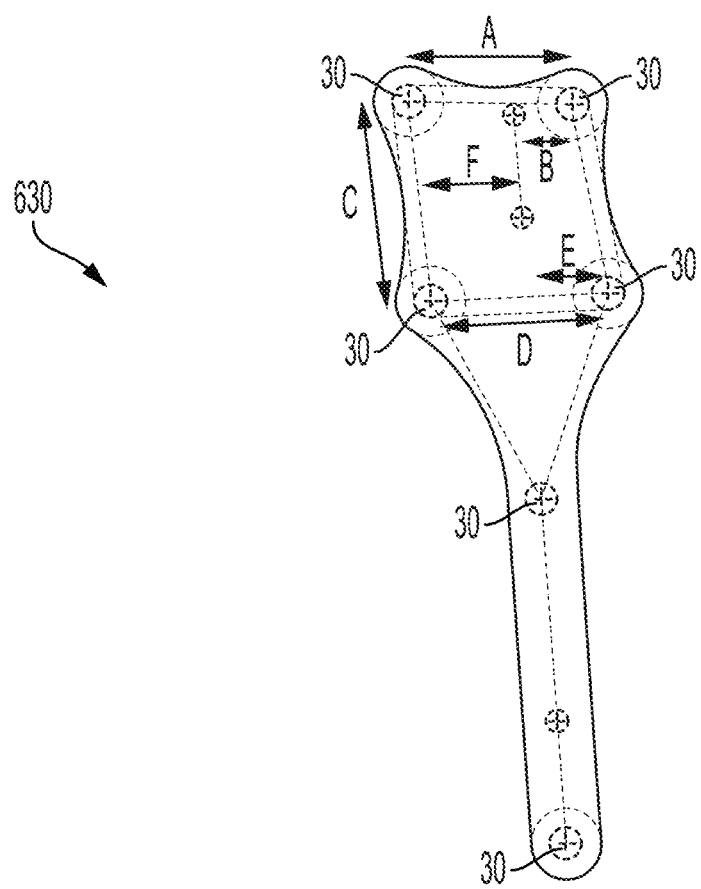
FIG. 15 shows a method to define minimum and maximum plate dimensions, as part of the pre-operative plan of FIG. 2
Figure 16:
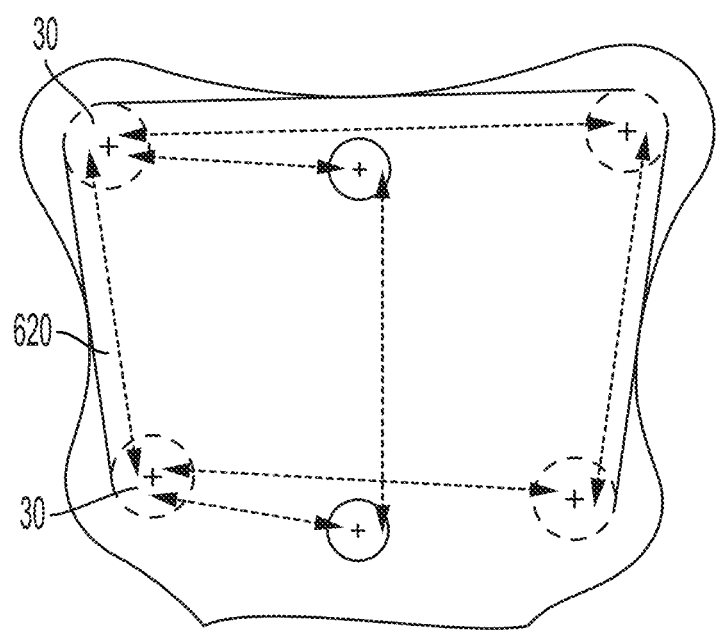
FIG. 16 shows boundaries calculated according to the method of FIG. 15.

To ensure sufficient clearance, the software application may enforce boundaries 620, i.e. minimum and maximum plate dimensions, based on the number and location of fixation holes 30. As shown in FIG. 15, boundaries 620 can be set based on a calculated maximum distance A,B,C,D,E, and F between each pair of fixation holes 30. Accordingly, the surgeon may not move a fixation hole (30) beyond boundaries 620 (FIG. 16).

To move a fixation hole 30 within boundaries 620, the surgeon can project a 2D sketch plane 630 showing profile 610 of the bone plate. Alternatively, the surgeon may pick three anatomic landmarks on the corrected bone model to place 2D sketch plane 630. It is beneficial to use a 2D sketch plane instead of a 3D sketch plane because it requires much less data processing and computing power.

Figure 17A:
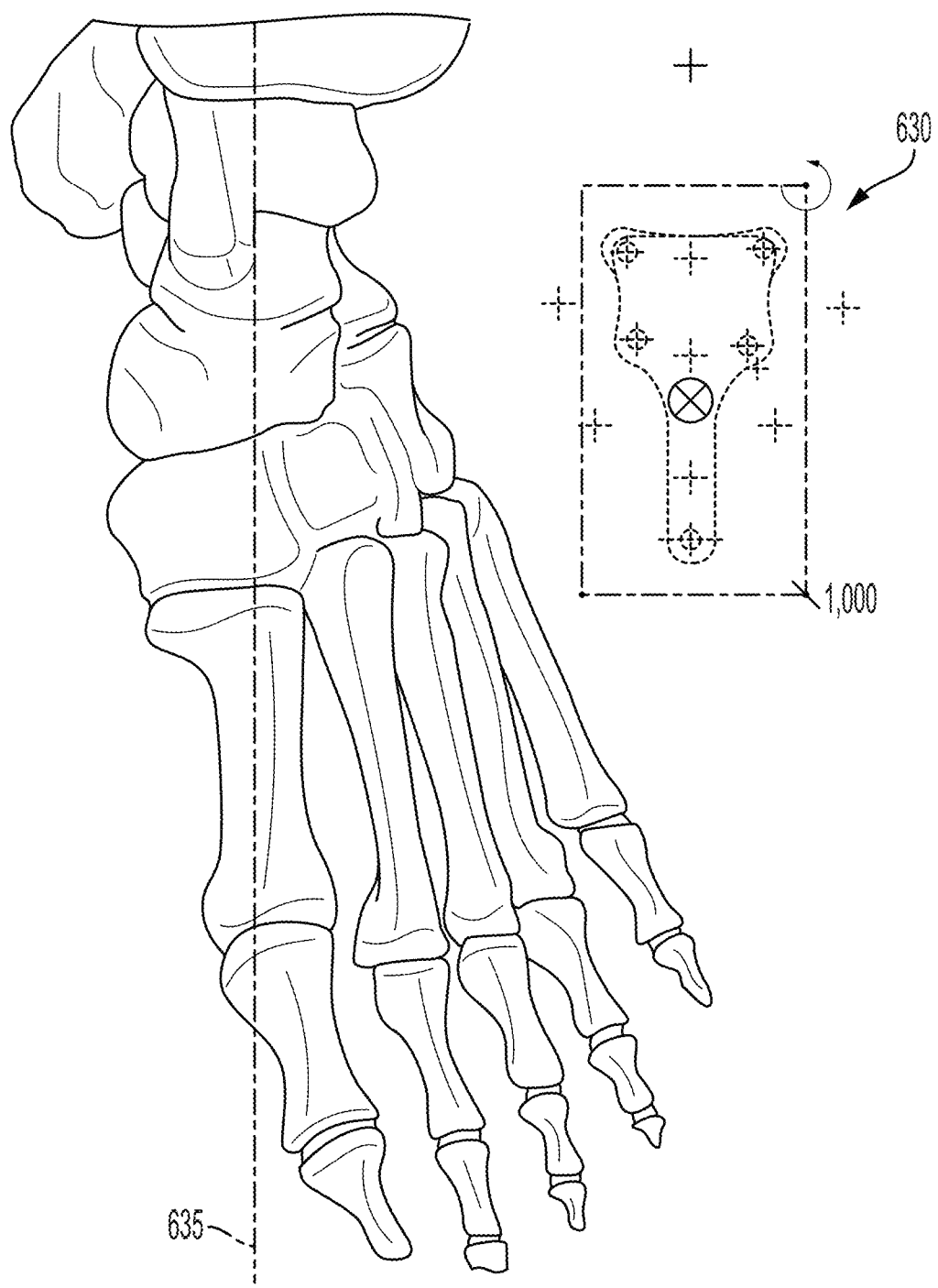
FIG. 17a shows one embodiment of a plate profile with minimum and maximum plate dimensions calculated according to the method of FIG. 15.
Figure 17B:
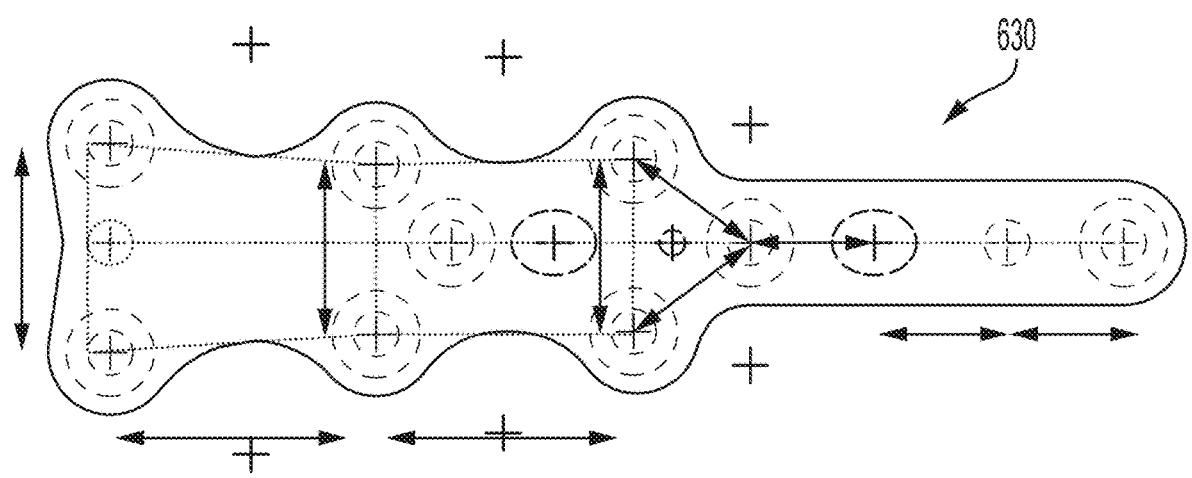

In 2D sketch plane 630, the surgeon can project profile 610 of the bone plate over the corrected bone model, as shown in FIG. 17a. By default, profile 610 of the bone plate may automatically align with sketch axis 635. An enlarged view of 2D sketch plane 630 is shown in FIG. 17b.

Figure 18:
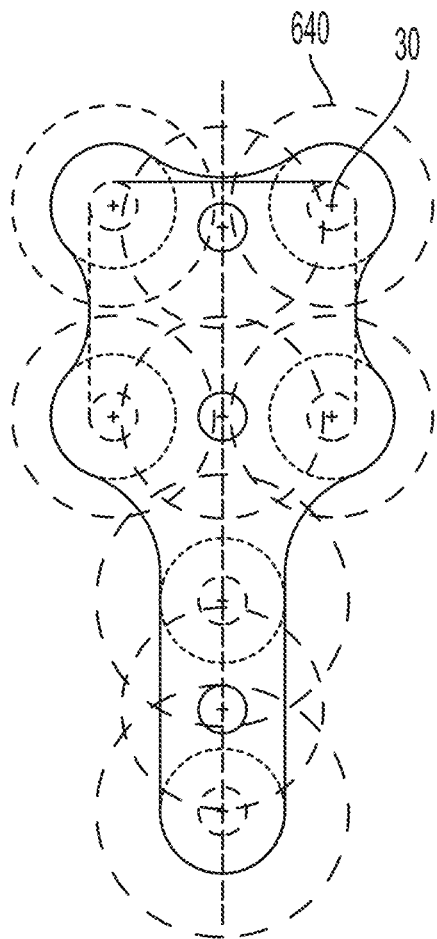
FIG. 18 shows minimum plate dimensions calculated according to the method of FIG. 15.
Figure 19:
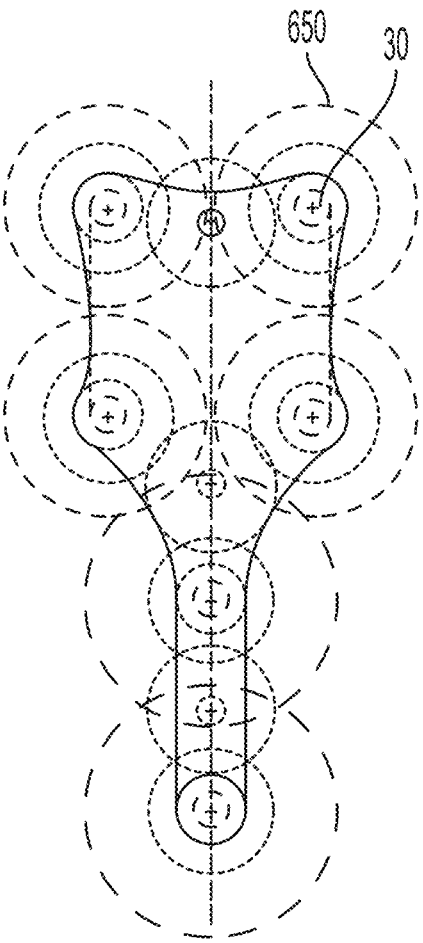
FIG. 19 shows maximum plate dimensions calculated according to the method of FIG. 15.

To facilitate the design process, the software application can show circles 640 with short dashes and circles 650 with long dashes around each fixation hole 30. Circles 640 can help show the minimum dimensions of the plate. As such, circles 640 for adjacent fixation holes 30 can either be tangent to each other or not touching each other (FIG. 18). To the contrary, circles 650 can help show the maximum dimensions of the plate. Circles 650 for adjacent fixation holes 30 can either be tangent to each other or overlapping each other (FIG. 19).

The dashed circles can be helpful because they can provide real-time visual feedback to the surgeon as he defines the number and location of fixation holes (30) within boundaries 620. In the software application, the surgeon can decide whether the dashed circles are visible sometimes, all the time, or not at all.

Figure 29:
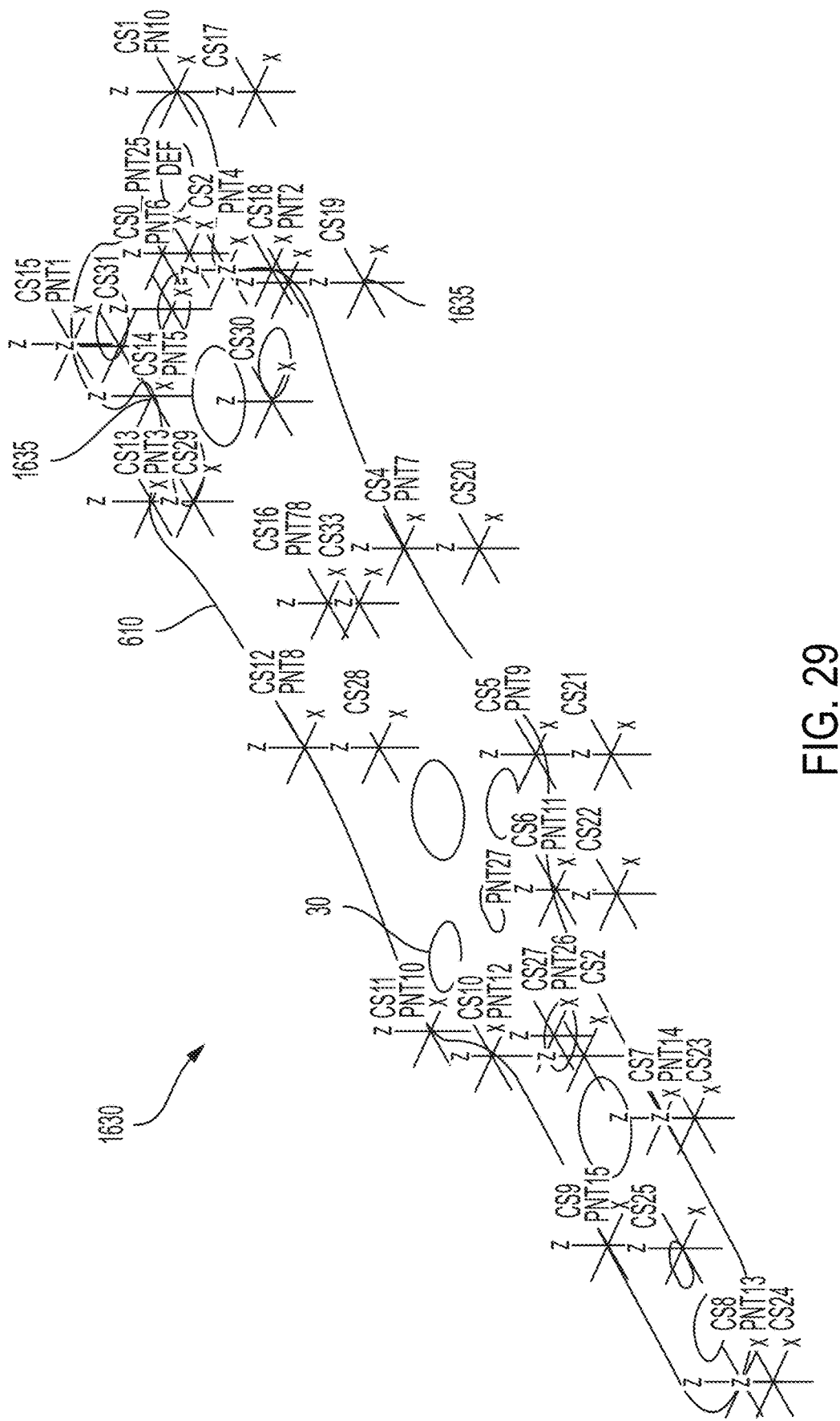
FIG. 29 shows another method to define minimum and maximum plate dimensions, as part of the pre-operative plan of FIG. 2.
Figure 30:
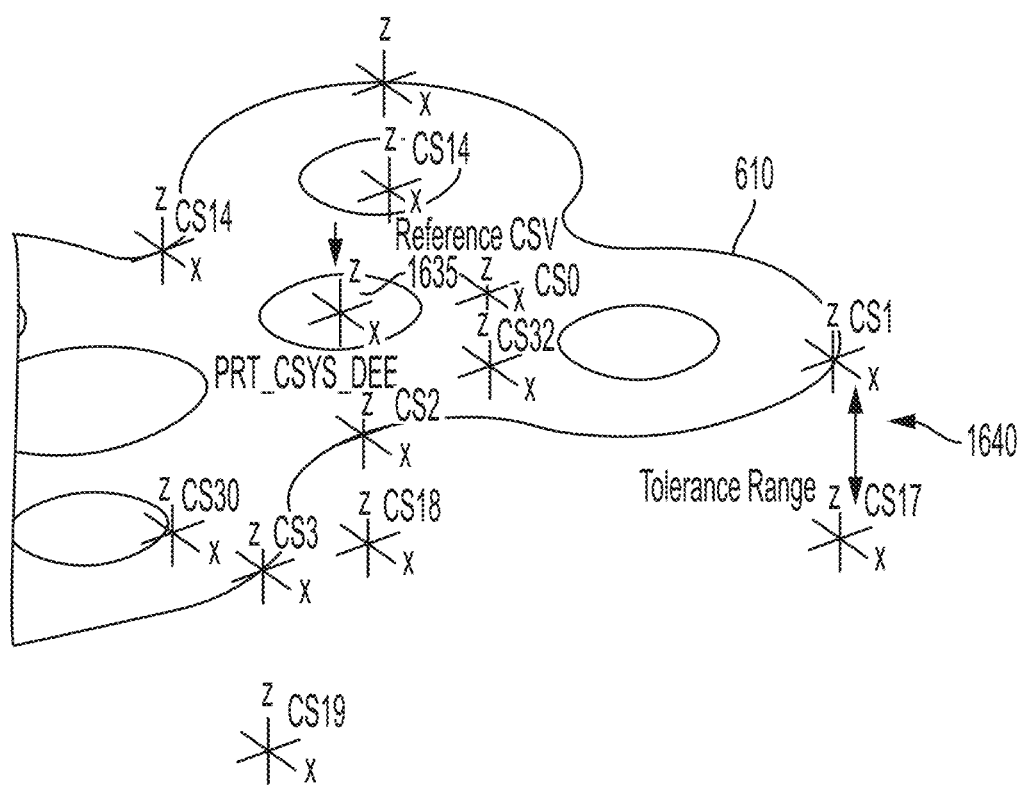
FIG. 30 shows tolerance ranges calculated according to the method of FIG. 29.

FIG. 29 shows another embodiment of a 2D sketch plane 1630 showing profile 610 of the bone plate. The 2D sketch plane 1630 includes reference markers 1635 surrounding the fixation holes 30 that can be used similar to boundaries 620. That is, each reference marker 1635 may have a predetermined tolerance range 1640 such that a fixation hole 30 cannot be moved beyond the minimum and maximum plate dimensions (FIG. 30).

As previously mentioned, it may be desirable to use fixation elements of different types or lengths and fixation holes of different sizes for different applications. For example, a bone plate may have at least one relatively large fixation hole adapted to receive a fixation element at a plurality of angles such that a fixation element could pivot during insertion. Accordingly, the size of the circles 640,650 or the tolerance range 1640 may vary among fixation holes 30.

Once the number and location of fixations holes 30 are defined, profile 610 of the bone plate may automatically regenerate. Now, the surgeon can translate, rotate, or otherwise manipulate profile 610 to better match patient bone anatomy. More particularly, profile 610 can be customized to better match the anatomy of the first and second bone portions 11, 12 in the corrected position in the 2D plane.

Figure 31:
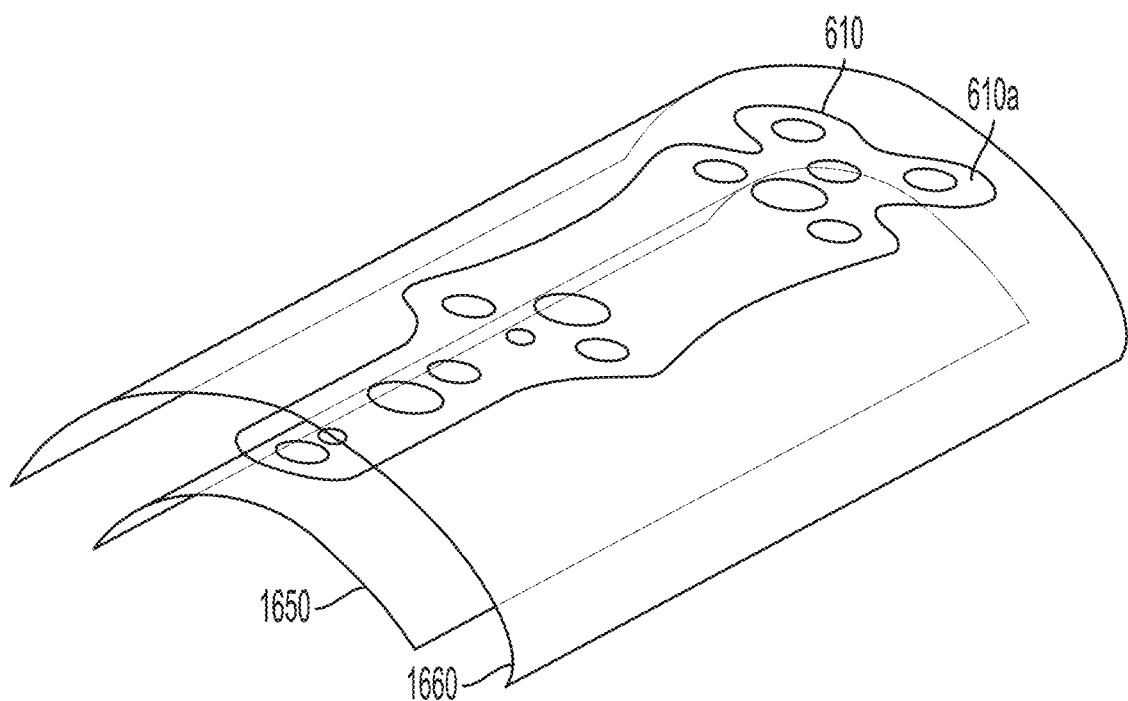
FIG. 31 shows yet another method to define minimum and maximum plate dimensions, as part of the pre-operative plan of FIG. 2.

After profile 610 is defined in the 2D plane, the surgeon may also use the software application to test its clearance in a 3D plane (FIG. 31). The software application may project a smaller proxy surface 1650 and a larger proxy surface 1660 over the profile 610 wherein the proxy surfaces 1650, 1660 correspond to the curvature of the corrected bone model. The smaller proxy surface 1650 may represent the maximum curvature for clearance while the larger proxy surface 1660 may represent the minimum curvature for clearance. Thus, the profile 610 may be customized so that it is disposed between the proxy surfaces 1650, 1660. This may help the bone plate 20 better match patient anatomy when the first and second bone portions 11, 12 are in the corrected position. For example, the surgeon can make sure that a portion of the profile 610a falls under proxy surface 1660; otherwise, portion 610a may "stick out" creating a gap between the bone plate 20 and the bone due to poor matching.

Figure 20:
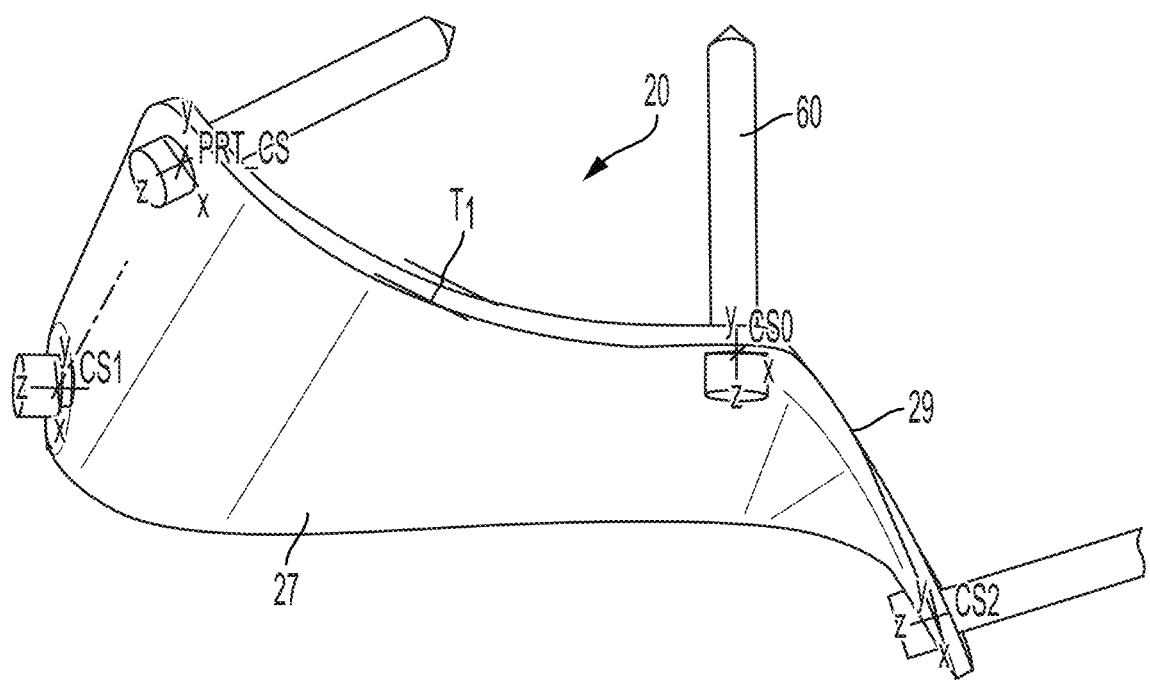
FIG. 20 shows one embodiment of a contoured plate with manipulated plate surfaces.

The surgeon can also drag and manipulate surface contours of inferior surface 29 of the bone plate to bend the plate in a 3D plane, as shown in FIG. 20. This can also help the surgeon design the bone plate to better match the anatomy of the first and second bone portions 11, 12 in the corrected position. Specifically, an inferior surface 29a of the first section 21 of the bone plate may correspond well with an outer surface of the first bone portion 11, and an inferior surface 29b of the second section 22 of the bone plate may correspond well with an outer surface of the second bone portion 12 (FIG. 14).

Furthermore, the surgeon can customize thickness $T_1$ of the bone plate. Thickness $T_1$ of the bone plate is defined by the linear distance between the superior and inferior surfaces 27, 29 of the bone plate (FIG. 20). In some embodiments, the thickness $T_1$ of the bone plate may vary along the first and second sections 21,22 to better match patient anatomy. Still, it is important that the bone plate can be thick enough to provide enough threads, or other fastening means, for proper alignment and fixation.

If the thickness of the bone plate is minimized, the surgeon may wish to include a protrusion on the superior surface 27 of the bone plate surrounding a fixation hole 30 in order to facilitate insertion of a fixation element. For example, a protrusion may create a support area to guide a fixation element into the fixation hole. A protrusion may also provide additional threads, or other fastening means, for proper alignment and fixation. When the surgeon is entering treatment information 100, the surgeon has the option to add these types of design notes 146 (FIG. 3).

Figure 21:
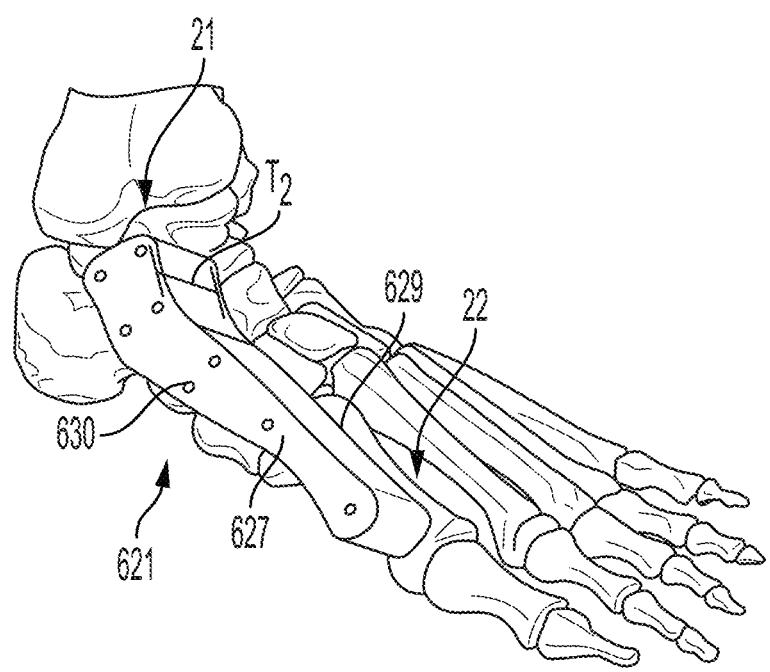
FIG. 21 shows one embodiment of a drill guide.

Sometimes the surgeon may require a drill guide for proper placement of the bone plate. As shown in FIG. 21, drill guide 621 includes a superior surface 627 and an inferior surface 629 that may be pre-operatively planned to match the patient's anatomy. Drill guide 621 also has a thickness $T_2$ defined as the linear distance between the superior and inferior surfaces 627, 629 of the drill guide 621.

Additionally, drill guide 621 has drill holes 630 adapted to receive a drilling tool. The location and orientation of drill holes 630 correspond to the location and orientation of fixation holes 30 on the bone plate 20. Thus, the angle of a drill hole 630 corresponds to the trajectory of the fixation element upon insertion. The software application can compute specific drill hole angle values based on the desired length of fixation elements in order to create a complementary drill guide. During computation of the drill hole angle values, the software application can also avoid interference between fixation elements and nerves. Thus, the resulting drill guide can be used to direct insertion of fixation elements at a pre-specified drill hole angle. When the surgeon is entering treatment information 100, the surgeon has the option to indicate a need for a drill guide 621 (FIG. 3). Thus, the software application can create a complementary drill guide according to the corrected bone model 620 (FIG. 2).

As a final step of pre-operative plan 80, the surgeon may review and approve a complete design for the patient-specific plating system 700 (FIG. 2). In the preferred embodiment, this may include simulating an operative technique on the corrected bone model. Moreover, in some embodiments, the simulation may be performed in the operating room such that any necessary patient-specific modifications can be made intraoperatively using, for example, additive manufacturing.

Figure 22:
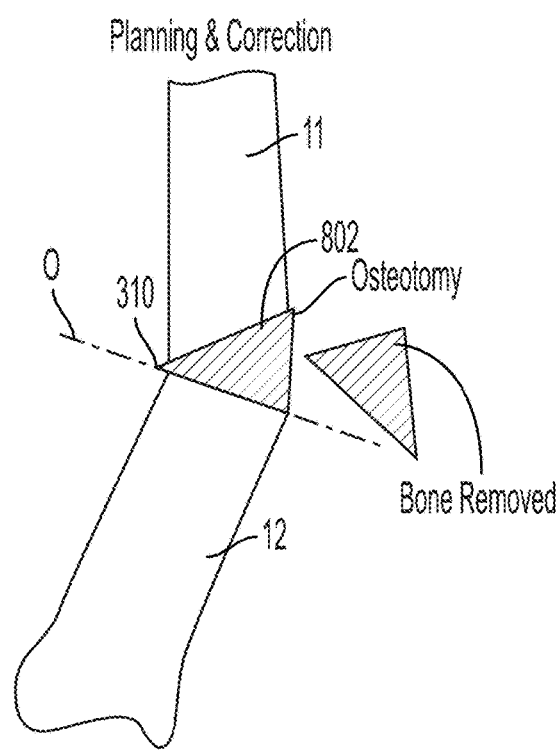
FIG. 22 shows one embodiment of visualizing an osteotomy, as part of the pre-operative plan of FIG. 2

At the start of the simulation, first and second bone portions 11,12 are in a deformed position with respect to each other. Then, the surgeon can calculate apex point 310 of the deformity and optionally perform an osteotomy to remove bone cut out 802. As shown in FIG. 22, the first bone portion 11 is above apex point 310 and the second bone portion 12 is below apex point 310.

Next, the surgeon can simulate positioning the customized bone plate 20 such that the inferior surface 29a of the first section 21 of the bone plate contacts the outer surface of first bone portion 11, and the second section 22 of the bone plate extends below apex point 310. As shown in FIG. 23, the surgeon may secure the first section 21 of the bone plate to the first bone portion 11 in the simulation. To do so, the surgeon could insert a first fixation element 60a through a first fixation hole 30a in the first section 21 of the bone plate, and into the first bone portion 11.

The surgeon may use additional fixation elements 60 to secure the first section 21 of the bone plate to the first bone portion 11. Heads 61a of the fixation elements in the first section 21 of the bone plate may be almost flush with the superior surface 27 of the bone plate.

Moreover, the surgeon can simulate inserting a second fixation element 60b through a second fixation hole 30b in the second section 22 of the bone plate, and into at least a part of the second bone portion 12 (FIG. 23). In many applications, the second fixation element 60b might be longer than the first fixation element 60a. Also, the second fixation hole 30b might be larger than the first fixation hole 30a. A large or elongated fixation hole may be desirable because it allows the fixation element to pivot during insertion.

Simulated actuation of the second fixation element 60b may cause the second bone portion 12 to rotate along the axis of rotation R for distance Θ such that first and second bone portions 11, 12 are in the corrected position with respect to each other. In the corrected position, the inferior surface 29b of the second section 22 of the bone plate contacts the outer surface of the second bone portion 12 (FIG. 24).

Once in the corrected position, the surgeon may use additional fixation elements 60 to secure the first and second sections 21,22 of the bone plate to the first and second bone portions 11,12. By the end of the simulation, heads 61 of all fixation elements may be flush with the superior surface 27 of the bone plate.

Figure 24:
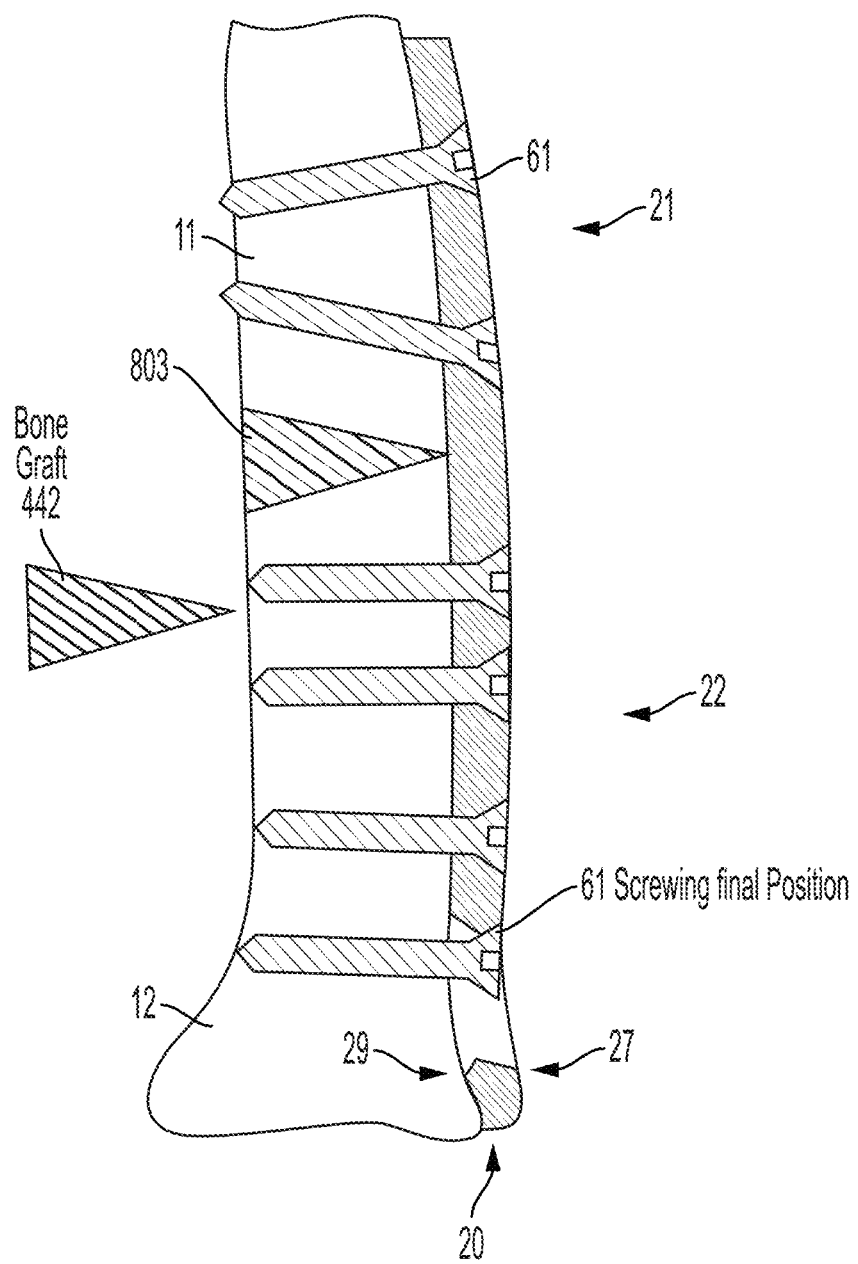
FIG. 24 shows one embodiment of visualizing a bone graft, as part of the pre-operative plan of FIG. 2

As shown in FIG. 24, the deformity correction created gap 803 between the first and second bone portions 11, 12 in the corrected position. Gap 803 is sized to receive bone graft 442, as previously discussed.

At this point, the surgeon can evaluate the customized details of the bone plate and make any desired changes to the patient-specific plating system before manufacturing. More particularly, the surgeon may alter the number or location of fixation holes, the orientation of fixation holes/elements, the type or length of fixation elements, the profile of the bone plate, the superior and inferior surfaces of the bone plate, the thickness of the bone plate, and/or any surface protrusions on the plate. For example, it may be particularly important for fixation hole 30b to be of sufficient size to allow the second fixation element 60b to pivot during actuation, as the first and second bone portions 11, 12 are arranged in the corrected position. The surgeon may also modify requests for a cut guide, a bone graft, and/or a drill guide.

Once the complete design for the patient-specific plating system is approved, a file including the design can be exported for manufacturing. Generally, the time between initiating a case request 100 and approval 700 may be approximately four working days (FIG. 2).

It is important to note that some steps of pre-operative plan 80 may be performed by a third party instead of the surgeon. For example, a Stryker design representative may perform the deformity assessment 300,350; deformity correction 400; bone density evaluation 500, 550; and plate customization 600 (FIG. 2). If a third party is involved, it is recommended that the surgeon pay careful attention to the design notes 146 when entering treatment information 100 (FIG. 3). It is also recommended that the surgeon carefully review and approve the complete design of the patient-specific plating system 700. In many cases, there may be correspondence between the surgeon and the third party regarding modifications to the customized bone plate before the system is approved.

Customized bone plate 20 of FIG. 1 can be created using a computer numerical control ("CNC") milling type operation or additive manufacturing. Body 23 of the bone plate can be made of a biocompatible material such as titanium or stainless steel.

The time for manufacturing may be approximately eight working days. Thus, the total time to create a patient-specific plating system would be, for example, approximately twelve working days.

Overall, a patient-specific plating system according to the present invention may provide better patient matching as a result of in-depth pre-operative planning. Also, the creation and use of a customized bone plate may offer significant improvements over standard bone plates.

Notably, the deformity assessment and correction tools described herein allow a surgeon to design a customized bone plate that can correct special situations or complex anatomy. With these tools, the surgeon can visualize both a deformed bone model and a corrected bone model. This may be useful when correcting Charcot, midfoot, and ankle deformities, as well as other types of bone deformity in other parts of the body.

Furthermore, the customization of a profile and inferior surface of a bone plate according to a corrected bone model can reduce pain and discomfort for the patient. This is because the profile and inferior surface of the plate may closely match the patient anatomy, particularly, the outer surfaces of the first and second bone portions in a corrected position.

Using a software application, the surgeon can also visualize relative bone densities. This allows the surgeon to customize the number and location of fixation holes in a bone plate such that the bone plate can be secured to higher density bone areas. This can promote healing because first and second bone portions can be properly aligned and secured in the corrected position.

Moreover, the software application can enforce predetermined boundaries to ensure proper dimensions of the bone plate given the number and location of fixation holes. This prevents the bone plate being too small or too large for a specific patient.

During pre-operative planning, the surgeon may also request: a complementary cut guide which may improve the accuracy of bone-cuts in an osteotomy procedure; a complementary bone graft assessment which can fill a gap between first and second bone portions in a corrected position; and a complementary drill guide which may facilitate plate fixation. The complementary cut guide may be especially useful because the inferior surface may be preoperatively planned to better match the patient's anatomy in order to help ensure proper placement of the cut guide. Thus, the surgeon may be able to make more accurate bone cuts, as well as multi-angle bone cuts when using a single cut guide.

In addition, the customized bone plate is desirable to surgeons because it is quickly realizable (in about two weeks) and easy to manufacture. After manufacturing, the customized bone plate may be included as part of a surgical kit for the surgeon. The surgical kit may further include at least two fixation elements, a cut guide, a bone knife, a drill guide, a drill, and/or a screw driver.

The method of using the patient specific plating system is also advantageous because the surgeon can gradually rotate the second bone portion into a corrected position with better precision, compared to existing methods. Although the method was described in reference to bone deformities in the foot, the same method could be applied to correct other deformities in other parts of the body.

The following paragraphs will now describe the selection and use of a prefabricated or standard bone plate. It may be desirable to use a prefabricated bone plate, rather than a semi- or fully-customized bone plate, in order to reduce the time and expense associated with the surgery. In many applications, a prefabricated bone plate will sufficiently hold the first and second bone portions in the corrected position for healing.

Figure 32:
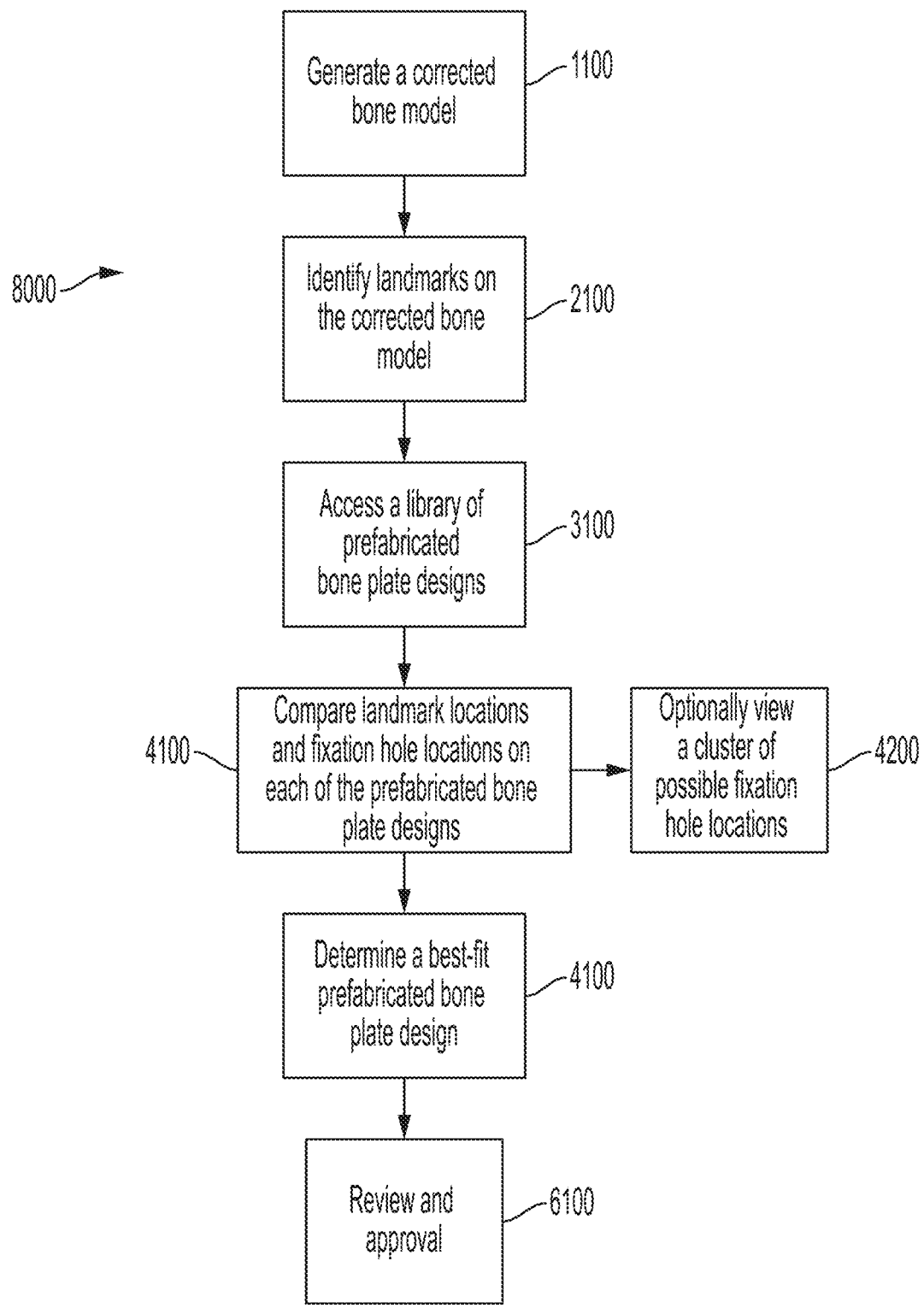
FIG. 32 is a block diagram depicting a pre-operative plan according to a second embodiment.

The selection process can involve detailed pre-operative planning One embodiment of a pre-operative plan 8000 is illustrated as a flowchart in FIG. 32. Similar to pre-operative plan 80 previously described, many steps of pre-operative plan 8000 also use a software application.

Figure 33:
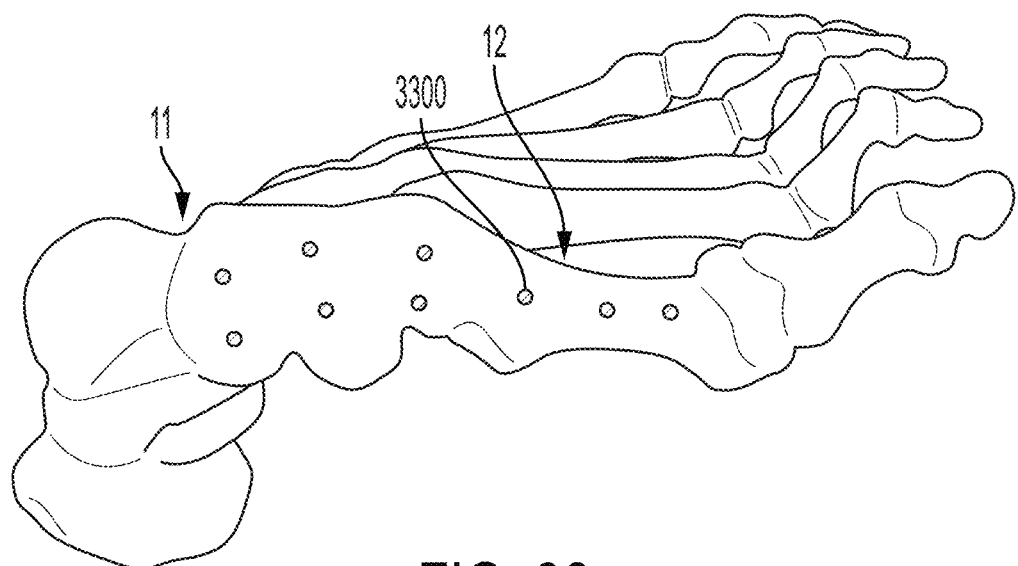
FIG. 33 shows one embodiment of generating a corrected bone model, as part of the pre-operative plan of FIG. 32.

First, a surgeon may generate a corrected bone model 1100, in order to identify landmark locations on the corrected bone model 2100. (FIG. 32). It is recommended that the surgeon choose at least three landmark locations 3300 on the bone model. As shown in FIG. 33, the surgeon has identified nine landmark locations 3300. Each landmark location 3300 is chosen to correspond to a desired fixation hole location 3310. Often, it would be desirable for the landmark locations 3300 to correspond to areas of the first and second bone portions 11, 12 having higher relative densities.

Figure 34:
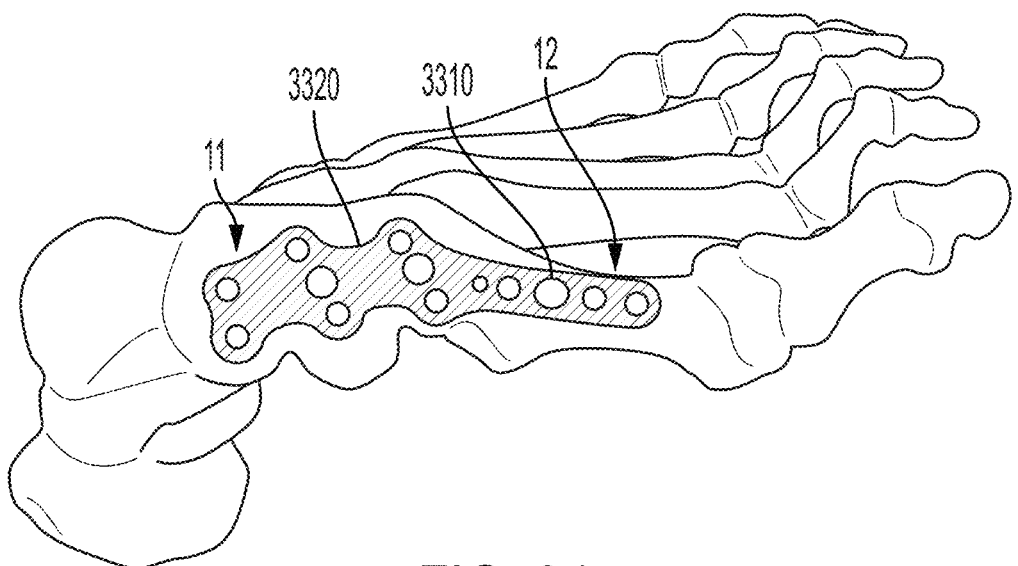
FIG. 34 shows one embodiment of identifying landmarks, as part of the pre-operative plan of FIG. 32.

Then, the surgeon can use the software application to access a library of prefabricated bone plate designs 3100. (FIG. 32). The library can hold several hundreds of prefabricated plate designs having different fixation hole location combinations. The software application can then be used to compare proximity of the landmark locations 3300 with the fixation hole locations 3310 on the various prefabricated plate designs 4100. (FIG. 32). To do so, the software application may calculate the average distance between each landmark location 3300 and each fixation hole location 3310 for each of the prefabricated plate designs. The lowest average distance would likely result in the best matching prefabricated plate design 3320. This plate design 3320 can then be projected onto the corrected bone model for 3D visualization and evaluation. (FIG. 34).

Figure 35:
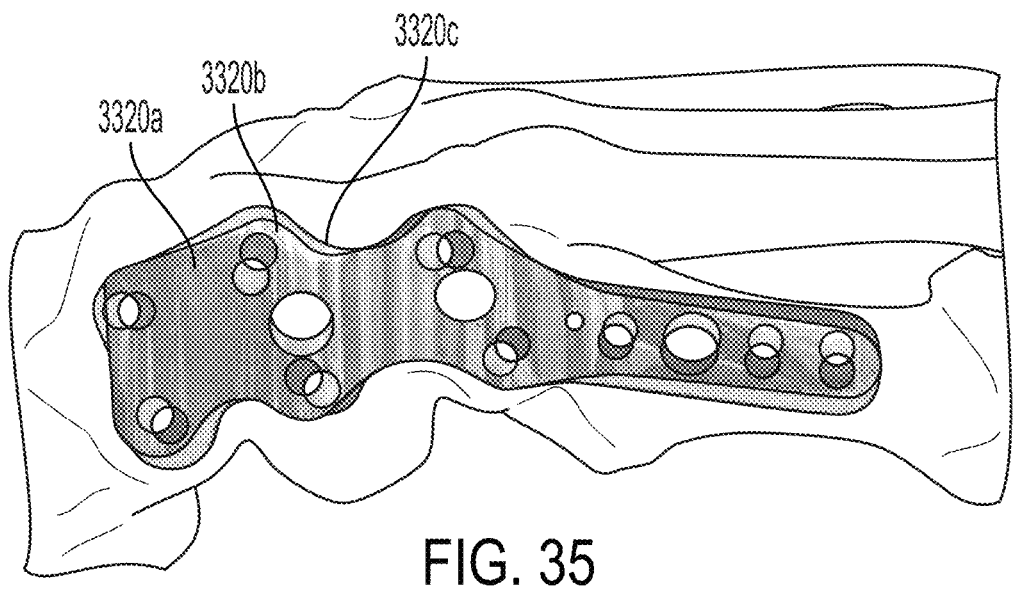
FIG. 35 shows one embodiment of determining a best-fit design, as part of the pre-operative plan of FIG. 32.

It is also possible for the software application to display a plurality of plate designs 3320*a-c* that have an average proximity within a predefined tolerance level that would be considered adequate for healing. (FIG. 35). Then, the surgeon could visually compare those plate designs and select the plate design with the best-fit.

Figure 36:
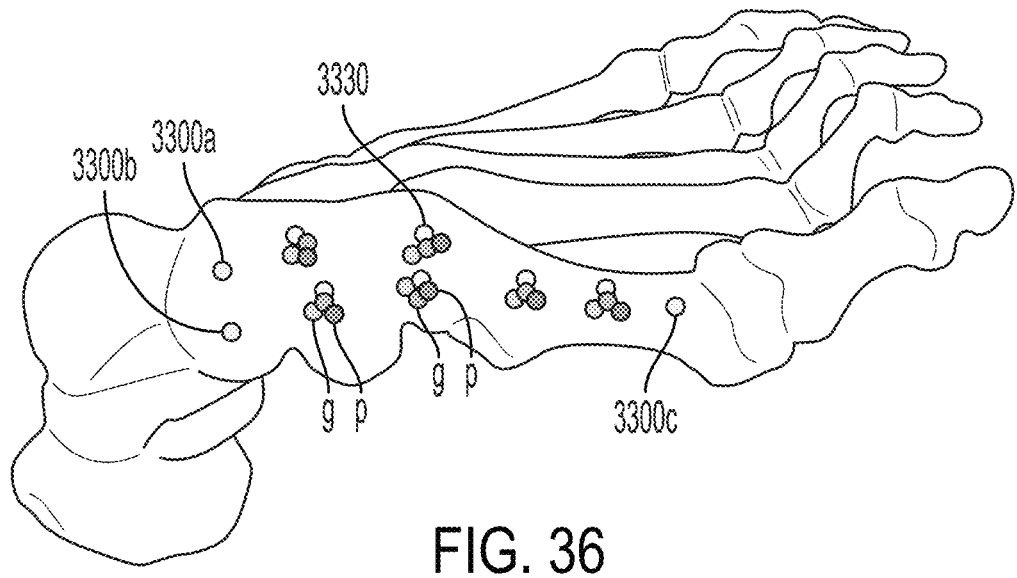
FIG. 36 shows one embodiment of viewing a cluster of possible fixation hole locations, as part of the pre-operative plan of FIG. 32.

Alternatively, the surgeon may only select three landmark locations. In such a case, it may be desirable for two of the landmark locations 3300*a-b* to be extreme proximal locations in the first bone portion and the third landmark location 3300*c* to be an extreme distal location in the second bone portion. (FIG. 36). These three landmarks 3300 could be "locked in" such that the software application will only display plate designs having fixation holes matching those landmark locations. The software application would then display a cluster 3330 of other possible fixation hole locations corresponding to the remaining possible plate designs 4200. (FIG. 32). As shown in FIG. 36, the three landmarks 3300*a*, 3300*b*, 3300*c* appear as a single option and could be colored, for example, in red; while six or more holes in between the extreme proximal and distal ends appear as a cluster of possible fixation hole locations. Here, each fixation hole location has three possible options corresponding to three possible plate designs. The options could be shown in grey scale or color-coded, for example, green options g for the green plate design; purple options p for the purple plate design; and orange options (not labeled) for the orange plate design. The software application may also provide an additional indicator for a suggested fixation hole location.

Figure 37:
FIG. 37 shows another embodiment of viewing a cluster of possible fixation hole locations, as part of the pre-operative plan of FIG. 32.

Next, the surgeon may choose a fourth landmark location from the options in one of the clusters. (FIG. 37). In response, the software application can automatically adjust the other possible fixation hole locations. Generally, the surgeon will continue selecting landmarks in order of decreasing significance until the best-fit plate is determined.

Depending on the patient anatomy, the available options may increase, decrease, or reposition as more landmarks are identified. For example, if the fourth landmark location is chosen at the suggested fixation hole locations; the first, second, and third landmarks may reposition or display a new cluster of green, purple, and orange options. Desirably, it is possible for the surgeon to change the landmark locations and/or prioritize the landmarks in real time.

Ultimately, the surgeon can select the best matching plate design based on the chosen landmark locations 3300. The plate design can then be evaluated for review and approval 6100 (FIG. 32). During evaluation, the surgeon can use the software application to simulate the correction procedure, in order to verify and test that the prefabricated plate design is adequate for healing, for example, within a predefined confidence interval.

Although the bone-contacting surface of the prefabricated plate would not be pre-operatively planned for a specific patient, the fixation hole location could still be optimized for the specific patient. Therefore, going through the selection process according to the embodiment described above would likely reduce patient pain and discomfort and/or promote healing.

The following paragraphs will now describe the creation and use of a semi-customized patient specific bone plate. A semi-customized bone plate may include some patient-specific features for better patient matching, while keeping resource costs low. It may also allow for design of the bone plate from information derived from 2D patient images such as X-rays as opposed to 3D bone models. The Stryker Orthopedics Modeling and Analytics system ("SOMA") is a population-based design environment featuring a large database of bone morphology, including size, shape, density, and inner and outer cortical boundaries, drawn from diverse populations. SOMA can be used in a combination with information derived from X-ray images of a particular patient in order to fill-in 3D information that is not available from 2D X-ray images. In such cases, SOMA in combination with X-ray images can be used to design an implant such as a bone plate that has both patient-specific and standard contact surfaces and fixation features.

In some applications, a prefabricated bone plate can be modified to provide better matching between the inferior surface of the bone plate and the outer surface of each of the first and second bone portions when the first and second bone portions are in the corrected position. In some cases, it may be beneficial to design a bone plate having both patient-specific and standard bone contact surfaces. Based on information that can be derived from patient images, there may be an ability to design a patient-specific contact surface for a portion of the bone plate, while selecting standard bone plate configurations and/or sizes for other portions of the bone plate. It designing a bone plate for the foot, it may be beneficial to include a polymer on a portion of the inferior surface of the bone plate, particularly at the talus. This may be desirable to minimize resistance during fusion of the joint. It also may be desirable to facilitate proper plate alignment and fixation.

Bone quality data may be derived from an image (or data relating to an image) of at least one joint. The image (or image data) can be obtained in a variety of ways, including by performing any medical imaging method known in the art, or by obtaining the image data from a collection and/or database. For example, the image data may be obtained by performing a CT scan. Additional suitable imaging methods include MRI, Electrical Impedance Tomography ("EIT"), Dual-Energy X-ray Absorptiometry ("DXA" or "DEXA"), X-ray, ultrasound, and nuclear imaging, for example. The image data may further comprise a combination of one or more different kinds of image data, for instance a composite image data that comprises both CT and MRI image data, for example.

The image data obtained may correspond to either a single individual or to a population of individuals. For instance, the image data may correspond to a joint of the individual for whom the press-fit is being optimized in accordance with the method(s) described herein. In this case, the parameters of the bone resection are being determined on a patient-specific basis such that the parameters optimize the press-fit between the individual anatomy and the articular implant. On the other hand, bone quality may be derived from data representative of a population, for instance a representative or average data corresponding to a particular population of individuals. The population may represent a class or sub-class of individuals, for instance members of an age-range, a gender, a class of individuals who suffer from a particular joint or knee ailment, any other suitable population that is relevant to articular implants, or any combination thereof. The SOMA database may be further used, for example, by normalizing a set of data relevant to the patient of interest onto a phantom tissue model. In this way, image data taken from a population may be used to derive the relevant bone quality and to optimize the engagement between the implant and the patient's bone.

Once the image data of at least one joint is obtained, bone quality information can be derived by a variety of methods for calculating or estimating bone properties from the imaging modalities previously described, including CT, X-ray, MRI, DEXA, etc. Such methods of deriving bone quality information are described in U.S. Pat. Pub. No. 2015/0080717 titled "Patient Specific Bone Preparation for Consistent Effective Feature Engagement," the disclosure of which is hereby incorporated by reference herein in its entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for correcting a deformity in first and second bone portions having a deformed position with respect to each other comprising:

a cut guide having a first portion fixable to the first bone portion and a second portion fixable to the second bone portion in the deformed position, the first and second portions being connected by a gear module having a pivot axis about which the first and second portions rotate to pivot the first and second bone portions about the gear module from the deformed position to a corrected position, the cut guide further having at least one cutting slot for resecting a bone cut out from at least one of the first and second bone portions; and a bone plate having a body including first and second sections and superior and inferior surfaces, the inferior surface having a preoperatively planned shape to match an outer surface of each of the first and second bone portions when the first and second bone portions are in the corrected position different than the deformed position.

2. The system of claim 1, wherein the inferior surface of the first section is adapted to contact the outer surface of the first bone portion above an apex point of the deformity and the inferior surface of the second section is adapted to contact the outer surface of the second bone portion below the apex point of the deformity when the first and second bone portions are in the corrected position.

3. The system of claim 1, wherein a thickness of the body defined by a linear distance between the superior and inferior surfaces varies from a first end adjacent the first section to a second end adjacent the second section.

4. The system of claim 1, wherein the bone plate defines at least one fixation hole in each of the first and second sections of the body.

5. The system of claim 4, wherein a location of each of the fixation holes is preoperatively planned to face areas of the first and second bone portions having higher relative density.

6. The system of claim 4, wherein one of the at least one fixation holes is adapted to receive a fixation element at a plurality of angles.

7. The system of claim 4, wherein one of the at least one fixation holes is larger than another of the at least one fixation holes such that a fixation element in the one of the at least one fixation holes is able to change angles during insertion.

8. The system of claim 4, further comprising:
a first fixation element insertable into a fixation hole in the first section of the bone plate and a second fixation element insertable into a fixation hole in the second section of the bone plate.

9. The system of claim 8, wherein the first and second fixation elements are different lengths.

10. A system for correcting a deformity in first and second bone portions having a deformed position with respect to each other, the system comprising:
a cut guide fixable to each of the first and second bone portions in the deformed position, the cut guide having a bone facing surface, an opposite surface and a cutting slot having a first portion with a first opening defined in the opposite surface and a second portion with a second opening defined in the opposite surface, the first portion and second portion being angled inwardly toward one another from the opposite surface toward the bone contacting surface, the second opening extending at a non-zero angle relative to the first opening such that a combination of the first and second openings approximately form a V-shape; and a bone plate having a body including first and second sections and superior and inferior surfaces, the inferior surface having a preoperatively planned shape to match an outer surface of each of the first and second bone portions when the first and second bone portions are in a corrected position different than the deformed position.

11. The system of claim 10, wherein the first opening and the second opening intersect at an intersection point.

12. The system of claim 11, wherein the cutting slot has a lower portion and an upper portion, the lower portion being defined by the first and second portions and the upper portion including a slot extending from the intersection point and away from the lower portion.

13. The system of claim 10, wherein the bone facing surface of the first section is adapted to contact the outer surface of the first bone portion above an apex point of the deformity and the bone facing surface of the second section is adapted to contact the outer surface of the second bone portion below the apex point of the deformity when the first and second bone portions are in the corrected position.

14. The system of claim 10, wherein a thickness of the body defined by a linear distance between the superior and inferior surfaces varies from a first end adjacent the first section to a second end adjacent the second section.

15. The system of claim 10, wherein the bone plate defines at least one fixation hole in each of the first and second sections of the body.

16. The system of claim 15, wherein a location of each of the fixation holes is preoperatively planned to face areas of the first and second bone portions having higher relative density.

17. The system of claim 15, wherein one of the at least one fixation holes is adapted to receive a fixation element at a plurality of angles.

18. The system of claim 15, further comprising:
a first fixation element insertable into a fixation hole in the first section of the bone plate and a second fixation element insertable into a fixation hole in the second section of the bone plate.

* * * * *